(12) United States Patent
Frankel

(10) Patent No.: US 10,234,666 B2
(45) Date of Patent: Mar. 19, 2019

(54) DEPTH ENHANCED AND FLUORESCENCE LIFETIME STIMULATED FLUORESCENT EMISSION FOR IN-VIVO IMAGING

(71) Applicant: Robert David Frankel, Rochester, NY (US)

(72) Inventor: Robert David Frankel, Rochester, NY (US)

( * ) Notice: Subject to any disclaimer, the term of this patent is extended or adjusted under 35 U.S.C. 154(b) by 650 days.

(21) Appl. No.: 14/949,612

(22) Filed: Nov. 23, 2015

(65) Prior Publication Data

US 2017/0102532 A1   Apr. 13, 2017

Related U.S. Application Data

(63) Continuation-in-part of application No. 14/881,701, filed on Oct. 13, 2015.

(51) Int. Cl.

| | |
|---|---|
| *A61B 5/00* | (2006.01) |
| *G02F 1/11* | (2006.01) |
| *G02F 1/35* | (2006.01) |
| *G02B 21/00* | (2006.01) |
| *G02B 26/10* | (2006.01) |
| *G02F 1/225* | (2006.01) |
| *H01S 3/094* | (2006.01) |

(52) U.S. Cl.
CPC ........ *G02B 21/0076* (2013.01); *A61B 5/0071* (2013.01); *G02B 21/0028* (2013.01); *G02B 21/0032* (2013.01); *G02B 21/0048* (2013.01); *G02B 21/0056* (2013.01); *G02B 21/0072* (2013.01); *G02B 21/0084* (2013.01); *G02F 1/11* (2013.01); *G02F 1/225* (2013.01); *G02F 1/3526* (2013.01); *H01S 3/094076* (2013.01); *A61B 5/443* (2013.01); *A61B 5/444* (2013.01); *A61B 2562/0233* (2013.01); *G02B 26/101* (2013.01); *G02B 2207/114* (2013.01)

(58) Field of Classification Search
CPC .............................. G01J 3/18; G02B 21/0076
See application file for complete search history.

(56) References Cited

U.S. PATENT DOCUMENTS

| | | | |
|---|---|---|---|
| 6,351,581 B1 * | 2/2002 | Doerr ................. | G02B 6/12021 385/24 |
| 2003/0179344 A1 * | 9/2003 | Van de Velde ......... | A61F 9/008 351/200 |

(Continued)

*Primary Examiner* — Dominic J Bologna
(74) *Attorney, Agent, or Firm* — Tarter Krinsky & Drogin LLP

(57) ABSTRACT

The specification relates to a microscopy system. The microscopy system includes a first laser emitting a first laser pulse, the first laser pulse being a pump beam; a second laser emitting a second laser pulse, the second laser pulse being a probe beam; time delay components for delaying the probe beam, wherein the time delay components delay the probe beam by 0.3 ps to 5 ns relative to the pump beam; an optical device for combining the pump beam and the delayed probe beam into a combined laser pulse, the combined laser pulse having a reduced focal spot size; a galvanometer scanning system for delivering the combined laser pulse to a focal spot in a focal plane, wherein the reduced focal spot size of the combined laser pulse initiates a stimulated emission of a targeted molecule, the stimulated emission having dipole-like backscatter, and a detector for detecting the dipole-like backscatter.

17 Claims, 10 Drawing Sheets

(56) References Cited

U.S. PATENT DOCUMENTS

| | | | |
|---|---|---|---|
| 2009/0279086 A1* | 11/2009 | Hell | G01N 21/64 356/318 |
| 2010/0238438 A1* | 9/2010 | Frankel | G01J 3/44 356/318 |
| 2011/0128538 A1* | 6/2011 | Cerullo | G01J 3/44 356/301 |
| 2017/0219489 A1* | 8/2017 | Cheshnovsky | G02B 21/00 |

* cited by examiner

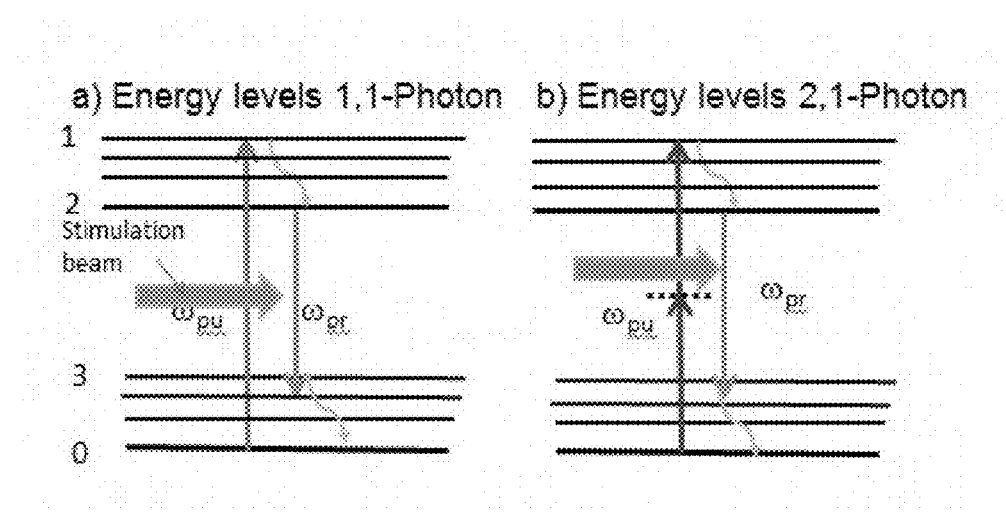
FIGURE 1a
FIGURE 1b
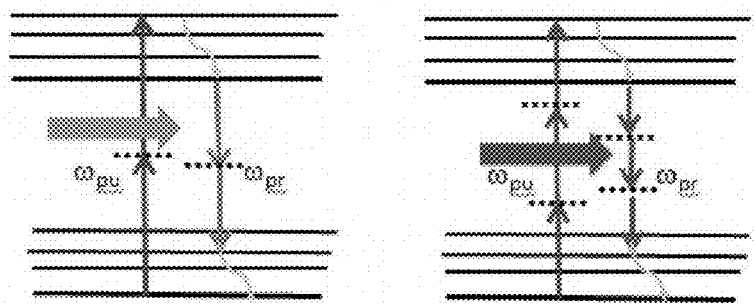
FIGURE 1c
FIGURE 1d

DEPTH ENHANCED AND FLUORESCENCE LIFETIME STIMULATED FLUORESCENT EMISSION FOR IN-VIVO IMAGING

BACKGROUND

This disclosed technology relates to stimulated emission fluorescence microscopy and more particularly to in-vivo stimulated emission.

There is significant interest in providing deep imaging for use in research, neuroscience, endoscopy, dermatology and intra-surgical definition of clear margins during removal of malignant tissues. For example, Optical Coherence Tomography (OCT) can obtain images up to 1 mm depth in tissue.

Multi-Photon Excitation (MPE) imaging can enhance the depth of penetration by using infrared photons for excitation where tissue absorption is low. MPE uses two or more photons to excite emission as shown in FIG. 1b. In MPE, the two or more photons can be simultaneously absorbed by one molecule, through the population of one, or more, very short lived virtual states.

MPE excitation has also been used in Fluorescence Lifetime Microscopy (FLIM), for example, to measure the fluorescent lifetimes of bound and free state metabolic cofactor NADH. Fluorescent lifetimes are of importance when determining a metabolic state of cells, in accessing tissue health and differentiating normal from malignant cells. MPE, however, is relatively slow because the fluorescent yield of free NADH is low, has a short excited state lifetime and needs photon counting to create a decay curve.

Standard fluorescence is an incoherent spontaneous emission process where emission of one or multiple photons causes fluorescent emission. In standard fluorescence, the incoherent spontaneous emission can be red shifted from the excitation and can be considered a dark field imaging technique. The measurement process for standard fluorescence is limited to background fluorescence and electrical noise.

Stimulated fluorescent emission (STEM) imaging is a coherent stimulated process (the energetics of which is shown in FIG. 1a) that uses two photons—a pump and a probe. The pump excites an electron into excited state S1 from ground state S0. A several hundred femtosecond delay, or more, is allowed for the decay of an excited state vibrational level into the lowest excitation level in the excited state manifold S2 via a Kasha decay process. Then a probe (or stimulated emission) beam causes the stimulated emission of a photon and the de-excitation of the electron to S3, which then rapidly decays via a Kasha decay process back to S0. The signal measured is a gain in the probe beam. STEM techniques have been used to image molecules that absorb strongly, but do not fluoresce efficiently such as oxy-hemoglobin, deoxy-hemoglobin, melanin, cytochromes and certain drugs.

STEM is a bright field technique where a signal is added to the forward propagating probe beam. The gain in the beam is $10^{-4}$-$10^{-7}$ (depending on concentration). Therefore, sophisticated electronic signal processing lock-in techniques are usually required to detect a small probe beam change. STEM imaging also uses moderate to high concentrations of molecules to image tissue at moderate to high speed. Unlike fluorescence imaging where emission occurs in any direction, the emission in STEM occurs in the forward direction. Therefore multiple scattering events are required to collect the signal at the tissue surface. STEM is best used for weakly absorbing and scattering tissues but the depth of imaging is limited and requires collection at a significant angle outside of the imaging aperture, eliminating the ability to do confocal imaging and degrading signal to noise ratio by collecting photons that scatter prior to reaching focus.

The natural fluorescent (or spontaneous) or single photon stimulated emission electronic transition wavelength is much shorter than the 2 or more multiphoton stimulated emission wavelength provided for by the disclosed technology. The natural fluorescent (or spontaneous) or single photon stimulated emission electronic transition wavelength is equal to the single photon stimulated emission energy divided by the number of photons used to make the transition.

SUMMARY

The disclosed technology relates to multi-photon fluorescence microscopy used to increase depth of focus in in-vivo fluorescence imaging and to reduce photo-bleaching of examined tissues. The disclosed technology can be applied to many application including to image the metabolism of cells in-vivo, cerebral metabolism, as well as stimulated emission from lipids, proteins, and nucleic acids and to provide label-less stimulated emission contrast imaging and fluorescence lifetime data from molecules in tissue with multiple component lifetimes.

In one implementation, a microscopy system can comprise: a first laser emitting a first laser pulse, the first laser pulse being a pump beam; a second laser emitting a second laser pulse, the second laser pulse being a probe beam; time delay components for delaying the probe beam, wherein the time delay components delay the probe beam by 0.1 ps to 10 ns or 0.3 ps to 5 ns relative to the pump beam; an optical device for combining the pump beam and the delayed probe beam into a combined laser pulse, the combined laser pulse having a reduced focal spot size; a galvanometer scanning system for delivering the combined laser pulse to a focal spot in a focal plane, wherein the reduced focal spot size, when three or more photons are used for both excitation and stimulated emission, of the combined laser pulse initiates a stimulated emission of a targeted molecule, the stimulated emission having dipole-like backscatter; and a detector for enabling imaging of the dipole-like backscatter.

The Point Spread Function (PSF) of a multiphoton microscope is the product of the number of photons used to image the emission molecules. In the multiphoton stimulated emission microscope, four or more photons are used to stimulate the emission creating a very small focal spot. When three photons are used to excite the molecule and also three photons are used in the emission, the six photons comprising the two multiphoton processes reduce the focal spot size in the axial direction to more length than the stimulating wavelength, causing stimulated emission in both the forward and backward direction.

In some implementations, at least two photons can be used for excitation and at least two photons are used for stimulation emission of a targeted molecule or sample. In some implementations, the stimulated emission of the targeted molecule can be significantly red shifted, or shifted towards the stimulating wavelength, by having the excited state fluorescent electronic transition to the ground state vibrational levels by a multiphoton stimulated transition of the molecule where the sum of the energies of the multiple lower energy stimulated emission probe photons are resonantly about equal to the energy of the fluorescent transition. That is, an electronic transition from an excited electronic state to a lower energy vibrational ground state is driven by the emission of 2 or more photons at the stimulated emission wavelength. In some implementations, the stimulated emission of the targeted molecule can be used to measure a metabolic state of cells deep within tissues via a measurement of a concentration of metabolic cofactors NADH and NADPH, in both free and bound states. In some implementations, the multiphoton stimulated emission occurs in proteins, or nucleic acids and is used as image tissues without stain. In some implementations the stimulated emission is used to measure the concentrations of melanin and its derivatives.

In some implementations, the time delay components can include an optical switch in the probe beam line to switch the probe beam between at least two delay lines. In some implementations, the optical switch can allow at least two different temporal delays between the pump beam and the probe beam so that molecular fluorescence lifetime can be calculated. In some implementations, the optical switch can be a Mach-Zehnder interferometer.

In some implementations, the combined laser pulses can be used to excite an electron into an electronic excited state that emit stimulated emission from its lowest energy excited state level.

In some implementations, the microscopy system can further comprise: an acousto-optic modulator for modulating the pump beam on and off. In some implementations, the collection apparatus can generate an imaging signal corresponding to a gain in intensity of the probe beam computed as the difference between the combined laser pulse with the pump beam on and the combined laser pulse with the pump beam off.

In another implementation, a microscopy method can comprise the steps of: emitting a first laser pulse, the first laser pulse being a pump beam; emitting a second laser pulse, the second laser pulse being a probe beam; delaying the probe beam, wherein the time delay components delay the probe beam by 0.3 ps to 5 ns relative to the pump beam; combining the pump beam and the delayed probe beam into a combined laser pulse, the combined laser pulse having a reduced focal spot size; delivering the combined laser pulse to a focal spot in a focal plane, wherein the reduced focal spot size of the combined laser pulse initiates a stimulated emission of a targeted molecule, the stimulated emission having dipole-like backscatter, and enabling imaging of the dipole-like backscatter.

In some implementations, at least two photons can be used for excitation and at least two photons are used for stimulation emission of a targeted molecule or sample. In some implementations, the stimulated emission of the targeted molecule can be significantly red shifted or shifted towards the stimulating wavelength. In some implementations, the stimulated emission of the targeted molecule can be used to measure a metabolic state of cells deep within tissues via a measurement of a concentration of metabolic cofactors NADH and NADPH, in both free and bound states.

In some implementations, the time delay components can include an optical switch in the probe beam line to switch the probe beam between at least two delay lines. In some implementations, the optical switch can allow at least two different temporal delays between the pump beam and the probe beam so that molecular fluorescence lifetime can be calculated. In some implementations, the optical switch can be a Mach-Zehnder interferometer.

In some implementations, the combined laser pulses can be used to excite an electron into an electronic excited state that emit stimulated emission from its lowest energy excited state level.

In some implementations, the microscopy method can further comprise the step of: modulating the pump beam on and off. In some implementations, the collection apparatus can generate an imaging signal corresponding to a gain in intensity of the probe beam computed as the difference between the combined laser pulse with the pump beam on and the combined laser pulse with the pump beam off.

An advantage of the disclosed technology is an enhancement of the depth and speed of metabolic imaging for use in research and clinical medicine.

BRIEF DESCRIPTION OF THE DRAWINGS

FIG. 1a is a graphical depiction of an energy diagram of 1 photon STEM;

FIG. 1b is a graphical depiction of an energy diagram of 2 photon excitation and 1 photon stimulated emission STEM;

FIG. 1c is a graphical depiction of an energy diagram of MP-STEM (2 pse);

FIG. 1d is a graphical depiction of an energy diagram of 3 photon MP-STEM (3 pse);

DETAILED DESCRIPTION

Figure 2:
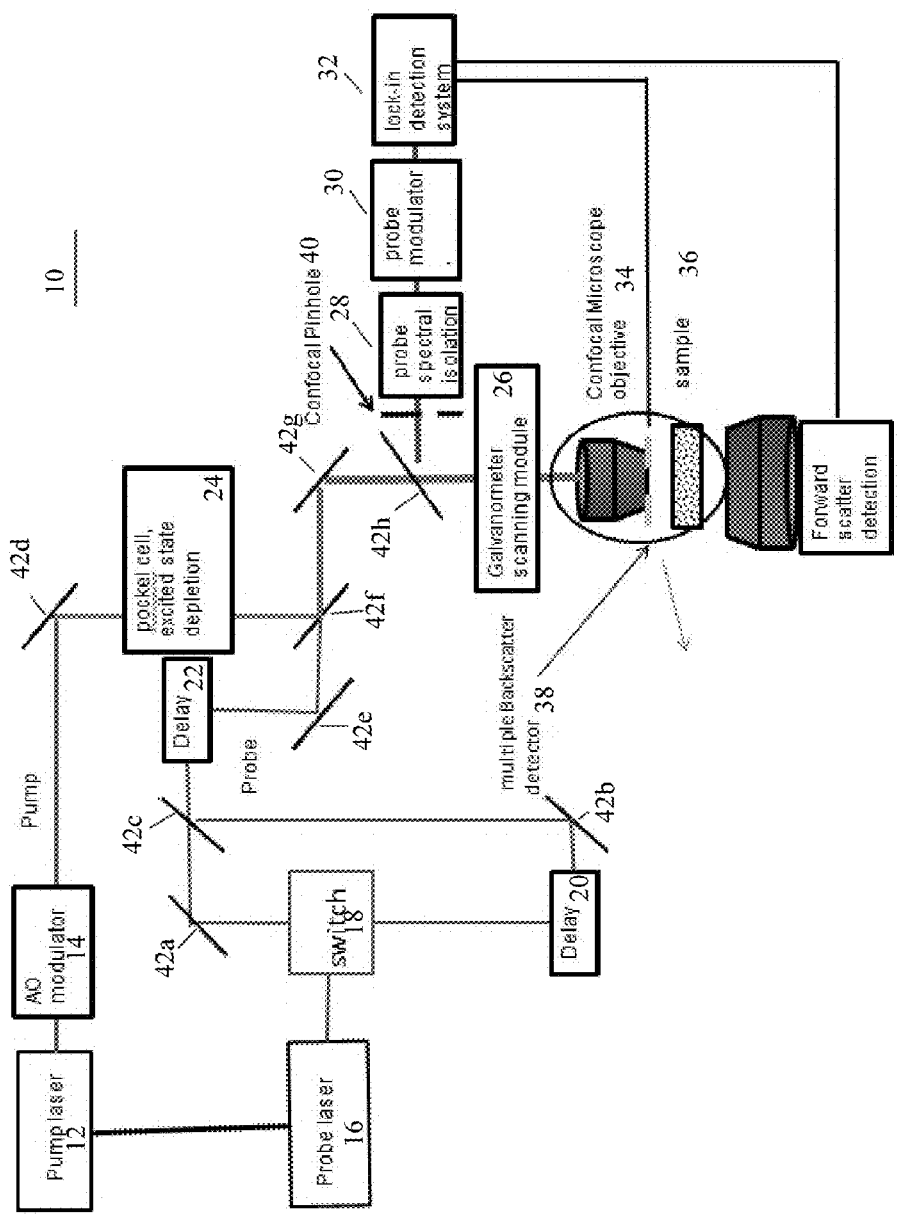
FIG. 2 is a block diagram of an example of a system used with the disclosed technology.

The disclosed technology is related to systems and methods that enable deep tissue imaging (in a range of about 0.5 to 5 mm or 1 to 1.5 mm) through the use of two or more photons to excite a molecule of a sample tissue through a virtual excited state. For example, stimulated emission photon beams with photons of ½, ⅓ OR ¼ of the energy difference of the lowest level excited state and an excited level in the ground state manifold can be used to stimulate 2, 3, or 4 photons that can be added to a stimulated emission beam. This emission can occur as the excited state electron is moved from the excited state to the ground state manifold through one or more virtual energy levels via a multi-photon stimulated emission process.

The disclosed technology also can use 3-4 photons for both excitation and emission, as well as, shrinking a focal axial diameter of a focal spot in a confocal geometry to subwavelength dimensions. This shrinking of the focal axial diameter enables significant back dipole-like backscatter emission and direct ballistic backscatter imaging from deep within tissues.

The disclosed technology can be used to measure the concentrations of both fluorescent and non or poorly-fluorescent states of the enzyme cofactors NADH and FAD, map the metabolic state of a tissue under study and map many chromophores that are not fluorescent.

The disclosed technology can also enable label-free in-vivo auto-fluorescent imaging for medical research, endoscopy, dermatology and define clear margins in cancer surgery using low and high quantum efficiency emitters. In one implementation, Multi-Photon Stimulated Fluorescent (MP-STEM) can enable enhanced depth of penetration of imaging of metabolic metabolites and direct fluorescent imaging of DNA, RNA and protein fluorescence in living tissue. That is, the MP-STEM process collects multiple backscattered photons around an imaging aperture or collects direct backscattered photons in the imaging aperture from a dipole-like emission created using 3 and 4 photon stimulated emission processes. In addition, forward scattered photons can be collected from thin organisms or tissue cultures. MP-STEM enables deep tissue imaging of weak, as well as, strong, fluorescent molecules emitted in both the visible and UV regions of a spectrum. In some implementations, MP-STEM can be a multiphoton process for both excitation and generation of stimulated emissions, which in turn, red shifts stimulated emission photons for enhanced imaging.

In another implementation, Stimulated Emission Fluorescent lifetime (seFLIM) can measure molecular fluorescent lifetime by measuring stimulated emission with variable delays, from 100 femtoseconds to 5 nanoseconds between pump and probe pulses. seFLIM can enable direct determination of bound and free molecular concentrations of molecules where the bound and free molecular lifetimes are different, such as NAD(P)H, FAD and molecular electron transport molecules. Also, with seFLIM, molecular metabolism can be measured for NAD(P)H since bound and free concentrations can be measured thereby determining cancer margins during surgery.

A single fluorophore emits stimulated emission into the backward illumination and forward propagating modes in to the stimulating mode with equal probability. Also, since the fluorophore is small relative to the optical wavelength it is known that stimulated emission gain length increases as backscatter quickly decreases. Although the gain in the stimulated field can be small, if the focal spot is small, as the probe beam propagates along the forward direction through the focal spot the stimulated emission photons add in phase, increasing the coherent traveling field. The stimulated emission in the back propagation direction adds out of phase as the incident beam propagates forward. Thus as the gain medium length increases, the backscattered stimulated emission photons from axially spatially separate fluorophores destructively interfere. The backscatter stimulated field quickly decreases over sub-wavelength dimensions.

It is desirable to maximize the direct backscattered signal. The background noise characteristics in STEM imaging of dipole emitters are significantly different in the forward and backscattered directions. In the forward direction the background noise is primarily from photons in the excitation probe beam and the accompanying photon noise statistics. This is also the case for collection of multiply scattered epi collected signals. For backward propagating dipole emission in a confocal microscope, the background noise comprises backscattered probe photons from within the focal volume of the microscope, and multiply scattered photons that enter into the confocal aperture system.

Most backscattered photons within the microscope focal spot come from refractive index (RI) gradients in the focal volume. This noise can be about $5 \times 10^{-4}$ of the incident beam, at the interface of cytoplasm and cell nuclei. Thus backscatter noise can be less than forward noise, reducing the incident flux for STEM imaging. In addition, by reducing the noise, lock-in data collection techniques may not be required.

In co-pending U.S. patent application Ser. No. 14/881,701, hereby incorporated by reference, 2 photon stimulated emission in conjunction with a third beam—the donut beam was used to reduce the focal spot to dimensions of the axial focal spot to less than 50% of the probe wavelength to cause stimulated emission in the backscattered dimension.

In the present disclosure, the disclosed technology does not use the donut beam.

This disclosure includes the following:
1) A method and system for 2 or multi-photon excitation and 2 or more multi-photon stimulated emission to cause stimulated fluorescent emission that is red shifted, or shifted towards the stimulating wavelength, compared to the standard blue or UV fluorescent emission. The wavelength is the stimulated emission wavelength (the fluorescent wavelength)/(the number of photons required to equal the transitions) or ($f(\lambda)=\lambda_{SE} \times n$). This is called Multi-Photon Stimulated Emission (MP-STEM) imaging. The method and system uses of ≥2 pump photons and ≥2 probe photons to reduce the focal spot size to enable direct dipole-like backscatter emission in high numerical aperture systems.
2) A method and system to measure fluorescent life by stimulated fluorescence techniques by changing the delay between the pump and probe beams. With two or more different temporal delays between the pump and probe beams, molecular fluorescence lifetime can be calculated. The more time delay samples, the more components of lifetime can be measured. This is called stimulated emission Fluorescence Lifetime Microscopy (seFLIM)
3) One or both the of techniques in 1 and 2 are used to measure the metabolic state of cells deep within tissues (in a range of about 0.5 to 5 mm or 1 to 1.5 mm) via the measurement of the concentration of the metabolic cofactors NADH and NADPH, in both free and bound states.
4) One or both the of techniques in 1 and 2 are used to image the shifted UV stimulated emission from proteins and nucleic acids in vivo to image cells without the use of stains.

The energetics of pump and a probe beams used in stimulated fluorescent emission (STEM) imaging are shown in FIG. 1a. The pump excites an electron to state S1 from S0. The excited electron decays to the lowest energy excited state S2 via a rapid Kasha decay process decay process. Then a probe (or stimulated emission) beam causes the emission of a photon and the de-excitation of the electron to S3, which then rapidly decay via a Kasha decay process back to S0.

Multiphoton excitation, as shown in FIG. 1b, is widely used in fluorescent microscopy to enhance the depth of penetration of excitation light and to reduce the photobleaching of molecules positioned out of focus.

Multiphoton stimulated emission takes advantage of the fact that the Einstein absorption and stimulated emission coefficients are similar. Multiphoton stimulated emission red shifts the blue and UV fluorescent emission into the green, red or near IR. Two photon stimulated emission (2 pse) energy levels are shown in FIG. 1c. FIG. 1d shows the energetics of three photon excitation and three photon stimulated emission (3 pse). Using 2 or more photons for both excitation and stimulation is called Multiphoton Stimulated Emission (MP-STEM) microscopy.

MP-STEM is distinct from all previous types of multiphoton microscopy. Each excited electron transition to the ground state vibrational manifold adds two stimulated emission photons to the probe beam used to measure gain in 2 pse processes. Each photon has about ½ the energy of the single photon transition. Three photons are added to the probe beam in a 3 pse process for each molecular stimulated emission. Each photon in 3 pse has about ⅓ the energy of the single photon transition.

Figures 4, 5:
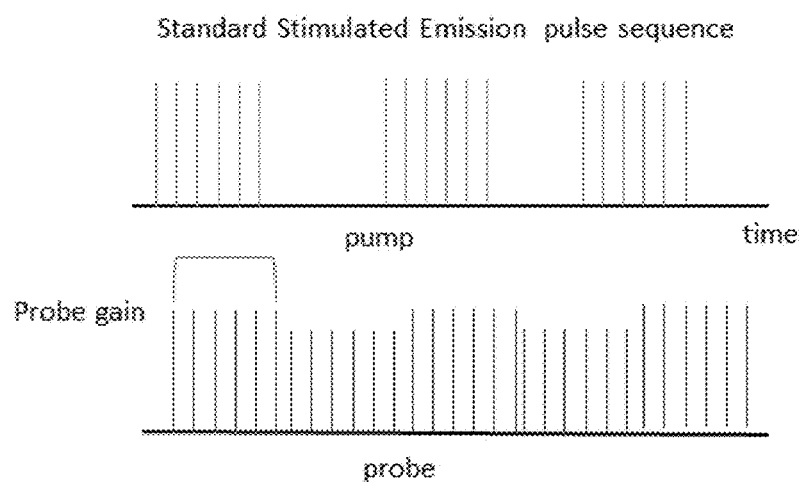
FIG. 4 is a graphical depiction of a time sequence for pump and probe beams.
FIG. 5 is a table showing 1 photon, 2 photon, 3 photon and 4 photon pump excitation and probe stimulated emission wavelengths for biological molecules.

Use of MP-STEM microscopy can enable direct in-vivo tissue imaging of the UV fluorescence from proteins and nucleic acids by shifting the emission into the green or red, as shown in the table in FIG. 5. This creates the opportunity for non-stained tissue contrast imaging at high resolution.

MP-STEM microscopy also produces stimulated emission focal Point Spread Functions (PSF) that are smaller than typical multiphoton fluorescent focal spots. This is because the PSF in MP-STEM is the product of 2n single photon PSFs, where n is the number of photons used in each the excitation or stimulate emission processes in the target fluorophore. In use, emission spots are reduced to less than 50% of the probe wavelength in the axial direction (see FIG. 6a) without the requirement of an annular beam.

Figure 9:
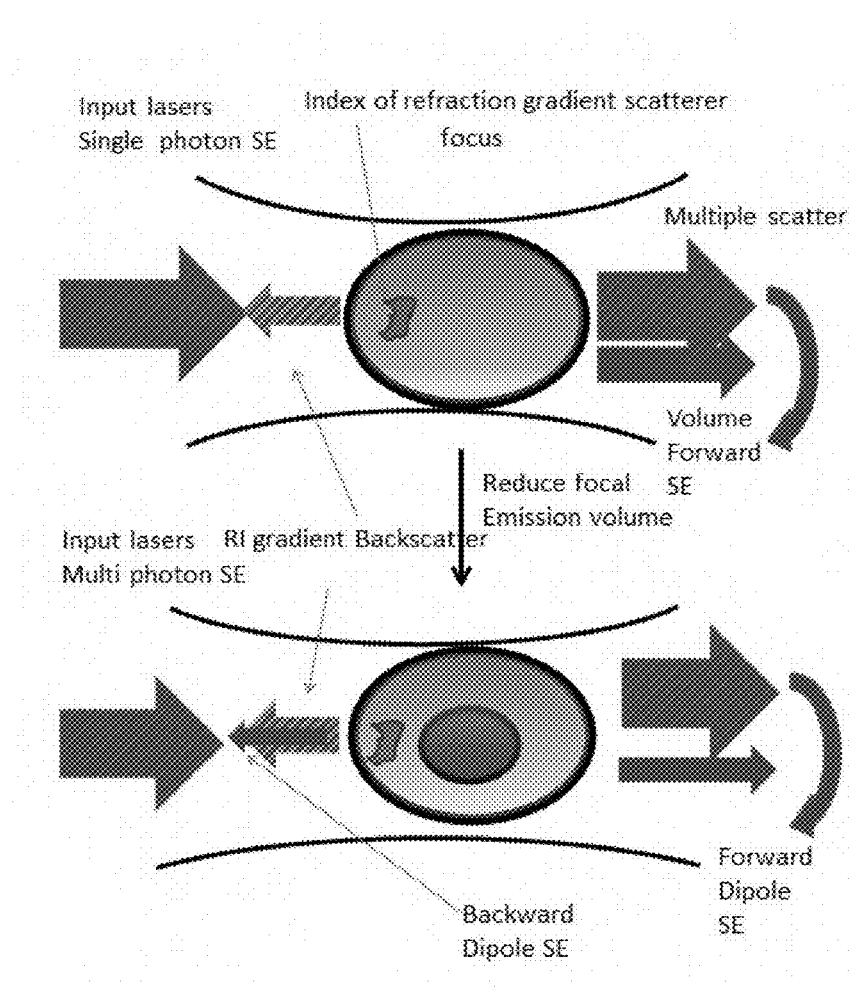
FIG. 9 is an illustration of a Position of Index of Refraction backscatter relative to focus and the relationship to Gouy phase.

When the emission spot is reduced to this length along the optical axis, forward propagating gain is converted to dipole-like stimulated emission with both a forward and backward scattered lobe as shown in FIG. 9. Backscatter occurs because of the lack of destructive interferometric cancellation of backscatter in gain lengths shorter than 50% of the emission wavelength. Direct backscatter enhances the recorded signal to noise ratio of images because of reduced backscatter noise compared to forward propagating noise due to the photon statistics of the propagating probe beam. Low noise can eliminate the need for lock-in recording techniques, and speed image acquisition of backscattered MP-STEM images.

MP-STEM systems operate near saturation where typically at most 50% of the excited molecules at focus will emit stimulated emission gain photons. STEM lasers systems have operated with very high repetition rate systems ~80 MHZ (12 ns pulse repetition rate) to build up SNR for lock-in detection of single photon STEM emission from rapid decay species, with imaging acquisition in the forward scattered direction or for multiple backscatter for collection in the epi direction. (Standard Multi-photon fluorescent systems operate at slower repetition, put higher intensities (near saturation) at focus.) At high repetition rates, near saturation local tissue heating can be an issue. Therefore lower repetition rates can be desired. However, in the backscattered direction repetition rates can be reduced because of the significant reduction in background photon noise.

At high repetition rates in MP-STEM systems, the excited state of long lived fluorophores may not be fully depleted when the next pump-probe pair arrives. For molecules with fluorescence lifetimes of >2 nsec, such as NADPH, this can be a problem. At least 4-6 fluorescent lifetimes between excitations can be allowed in order to depopulate the excited states.

In another implementation, methods and systems are introduced that use multiphoton STEM to measure the fluorescent lifetime of molecules with multiple decay constants. This method is called stimulated emission Fluorescent Lifetime Microscopy (seFLIM).

In STEM, the pump pulse can precede the probe pulse by at least several hundred femtoseconds to allow the decay of an excited state vibrational level into the lowest excitation level in the excited state manifold via a Kasha decay process. In seFLIM, the time delay between the pump and probe beams can be varied by significantly larger values. The probe delay, $\Delta t_{pr}$, can range from 0.3 ps-5 ns.

Figure 11:
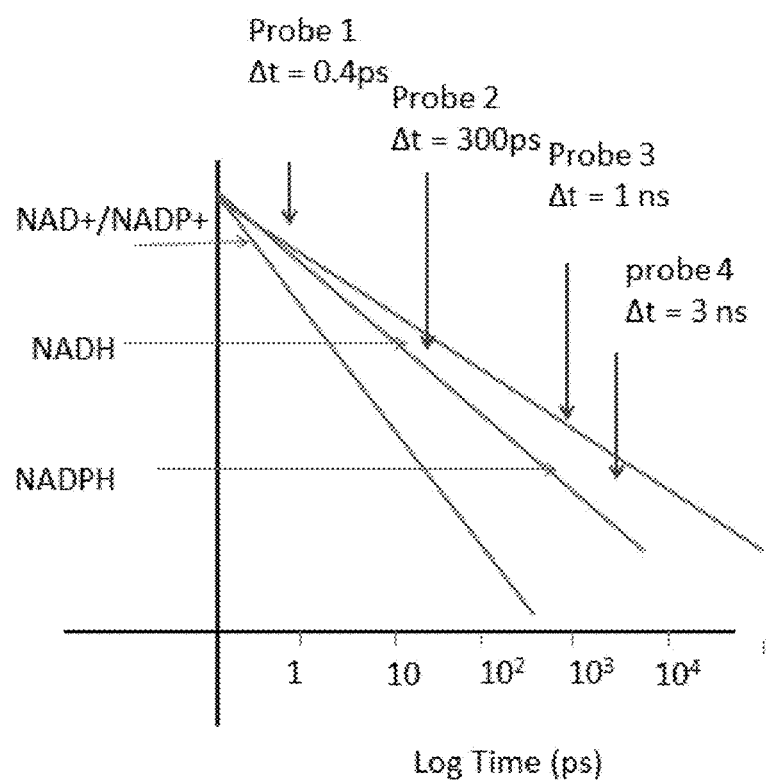
FIG. 11 is a graphical depiction of pulse timing of Stokes pulses relative to variable fluorescent lifetimes for free and bound NAD(P)H.

As shown in FIG. 11, multiple probe delays will sample different time marks on a fluorescence decay curve. Two sample points determine the fluorescence lifetime if there is a single exponential decay of a fluorescent species. These two time marks are used to determine two unknowns, $I_0$, the initial fluorescence decay intensity and $\tau_f$, the fluorescence decay constant. $I_0$ is proportional to the concentration of the fluorophore.

In seFLIM, the intensity of the pump laser can drive the fluorescent molecule close to saturation. At this intensity, close to 50% of the fluorescent molecules at focus are in the excited state S1 and the rest in the ground state S0. During the 0.-1 psec before the arrival of the probe pulse the excited electrons decay into lowest excitation state S3, leaving a population inversion in the fluorescent molecules at focus. The probe beam intensity can be enough to drive gain from close to 50% of the excited molecules into S3 and add photons into the probe focal modes.

If m multiple exponential decays are present, then 2 m time marks are required to reconstruct the m exponential decay constants and concentrations of m species of emitters. FIG. 11 shows multiple time marks that can be used for measuring the fluorescence from bound and unbound NADH and NADPH. If the time constants are approximately known in advance, fewer time points may be used to reconstruct the ratio of intensities, and hence the concentration of the lifetimes of the fluorescent species under study. For multiple decay constants, it can be assumed the first time point at ~0.3-1 ps measures the sum of the initial fluorescent intensities of all of the fluorescent species.

A variable delay can be introduced in the probe line to alter the interval between the time of arrival on the pump and probe as shown in FIG. 2. To maximize signal acquisition speeds, the delays can be switched as rapidly as possible. This can be done in the probe beam line by electronically switching pulses between different pathlengths as shown in FIG. 2. This enables full seFLIM imaging acquisition in a single image scan.

Imaging cellular metabolism is one application of seFLIM. A variable delay between the pump and probe pulses is introduced. This enables the measurement of cellular metabolism by determining the concentration of membrane bound and un-bound NADH and NADPH via lifetime determination. Rapid imaging of these compounds is possible since they are present in milli-molar concentrations. The number of NAD+ per cell in an astrocyte cell line has been measured to be greater $670 \times 10^{-18}$ ($4.0 \times 10^8$ molecules) moles and the number of NADH molecules per cell $110 \times 10^{-18}$ (0.7×10⁸ molecules). High natural concentration of molecules enables rapid seFLIM, especially in the epi direction for dipole-like scattering from sub-wavelength focal spots.

To measure NADPH and NADPH fluorescent lifetimes the optimum wavelengths are shown in FIG. 5. For 2 pse the pump and probe wavelengths are 680 nm and 920 nm, respectively. For 3 pse the wavelengths used are 1020 nm and 1380 nm respectively. For 4 pse the wavelengths used are 1380 nm and 1820 nm respectively.

seFLIM imaging can be used more deeply with 3 pse and 4 pse. Assuming imaging down at 3 absorption depths, 3 pse imaging can operate down to 800 microns and 4 pse at >1000 microns. Above 1000 nm the photon damage limit in tissues is higher, enabling higher intensity focal spots. The focal spots can be smaller enabling enhanced dipole backscatter. Fiber lasers can be used for excitation and stimulated emission. Use of fiber lasers reduces the cost of system construction, and enhances ease of use. Tissue dispersion is lower above 1000 nm than below, making achieving a more precise focal spots with short pulses easier to achieve.

The fluorescent molecule energy level diagrams for STEM imaging are outlined in FIG. 1a. In STEM, two laser beams at the pump frequency, $\omega_{pu}$, and probe frequency, $\omega_{pr}$, are coincident on a sample as shown in FIG. 1a. The pump photon excites an electron into state S1. This exited stated decays via a Kasha process to the lowest level excited state S2 in 0.1-1.0 ps. The probe frequency photons have appropriate energy to drive an excited electron into a high level excited state in the ground state manifold S3 as shown FIG. 1a. The electron in the ground vibrational excited state then losses energy as it decays into the lowest ground state S0 by another Kasha process.

FIG. 1b shows the excitation of the fluorescent molecule into the electronic excited state via a 2-photon excitation process. The electronic excited state excitation occurs through a virtual level intermediate, which has a femtosecond lifetime. Therefore, the two excitation photons arrive close in time, which requires high photon intensities and occurs at high probability at the focal spot of the microscope, using high power picosecond or sub-picosecond laser pulses. Advantages of 2-photon excitation can include 1) the lower energy photons used in 2-photon excitation generally have lower absorption and scattering cross-sections than the 1-photon excitation energies, enabling deeper tissue excitation; 2) the requirement of high intensity of excitation enables emission mostly from the focal volume; 3) the lower energy photons produce less photo-bleaching molecules in the focusing and defocus cones of the microscope objective, providing significantly less damage to the tissue being imaged.

FIG. 1c shows the energetics of a 4 photon MP-STEM process disclosed here. In this case 2-photon excitation and 2-photon stimulated emission are used. The addition of 2-photon stimulated emission along with 2-photon excitation is enabled by the approximate equivalence of the Einstein absorption and stimulated emission constants. The system is efficient when both the excitation and stimulated emission processes operate near saturation. This process is called 2 photon stimulated emission (2 pse) MP-STEM.

The addition of 2-photon stimulated emission has several advantages including; 1) significantly less absorption, and scattering of stimulated emission photons, enabling rapid and deeper stimulated fluorescent imaging; 2) enables forward and backscattered STEM imaging of fluorescent transitions in the UV, which normally would not be observable because of tissue absorption; 3) enables imaging of short lived fluorescent molecules such as DNA and proteins.

FIG. 1d shows the energetics of 6 photon MP-STEM process, which is also disclosed here. In 3-photon excitation and 3-photon stimulated emission there are 2 intermediate virtual levels. Therefore the required incident laser intensities can be higher than in 2 photon excitation and 2 photon stimulated emission. However, the process enables incident photons in the near infrared, for UV or blue fluorescent transitions from deep within tissue. This process is called 3 photon stimulated emission (3 pse) MP-STEM. Four photon stimulated emission (4 pse) MP-STEM is also possible.

Referring to FIG. 2, a microscopy system 10 focuses a pump beam from a pump laser 12 and a probe beam from a probe laser 16, both emitting laser pulses with a Gaussian beam profile and picosecond or sub-picosecond duration into diffraction limited spots in the focal plane of a high numerical aperture (NA) microscope objective 34. The pump and probe beams can be produced by fiber lasers, or solid state lasers such as a Ti:Sapphire laser. The lasers beam photons can be in the green through near infrared regions of the optical spectrum and broader (300-2000 nm or 500-1840 nm). A galvanometer scanning module 26 moves the focal spot around in the X,Y plane. A sample 36 to be investigated is located in or near the focal plane. The laser pulse is used to excite an electron into the electronic excited state that will emit stimulated fluorescent emission from its lowest energy excited state level.

The stimulated emission microscope system described here is a bright field imaging system and the intensity of the background probe radiation can be calibrated on a rapid time interval cycle. Therefore, the pump beam has an optical modulator 14 that turns the pump beam on and off enabling collection of probe beam photons with and without probe beam gain from stimulated emission. This can be an acousto-optic modulator 14.

The time sequence of the pump and probe beams are shown in FIG. 4. The pump is turned on for a series of pulses to measure gain and turned off to measure the bright field single without gain. The repetition rate of the pump and probe can be about 5-40 MHz or 10-20 MHz. The lock-in amplifier system 32 illustrated in FIG. 2 measures the envelope frequency of the pulse train at about 1-5 MHz.

Figure 10:
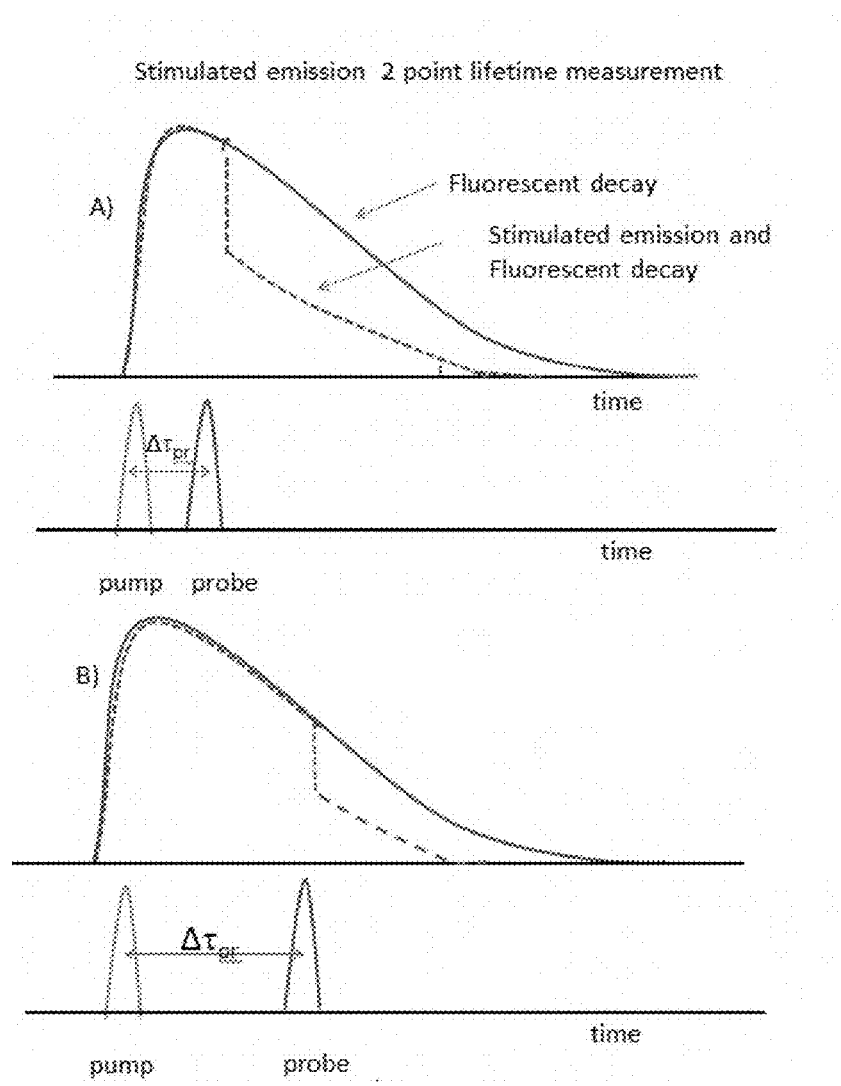
FIG. 10 is a graphical depiction of a time relationship of pump and probe pulses in stimulated emission FLIM (se-FLIM) imaging.

The pump beam can be delayed from 100s of femtoseconds to multiple nanoseconds after the arrival of the pump beam. The delay of the probe relative to the pump is shown in FIG. 10. This delay can be generated by a delay 20, 22 in the probe beamline or by electrical delay in the trigger circuit used in time synchronization of the pump and probe pulses. The pathlengths of the probe can initially be adjusted by placing an optical delay 20, 22 with movable mirrors in the laser beams, as illustrated for the probe beam. Long time delays can be used when the system is used to measure fluorescence lifetime of biomolecules.

Multiple delays are required to measure a multi-component exponential delay curve, as shown in the example of NAD(P)H in FIG. 11. One can measure multiple seFLIM delays at each pixel as the laser is scanned, in order to enhance image acquisition speed. This is accomplished by using an optical switch 18 in the probe beam line to switch the pulse between two or more delay lines 20, 22. FIG. 2 illustrates two separate probe beam lines. The optical switch 18 can be a Mach-Zehnder interferometer, if fiber optic lasers are used, or it can be an acousto-optic modulator or Pockels cell 24 if free space optical beam paths are implemented.

The pump beam is modulated on and off by an acousto-optic modulator 14. The pump laser beam and the probe laser beams are combined using conventional optics 42a-h, such as reflective and dichroic mirrors, beam splitters and lenses, or by fiber optical beam combiners.

Figure 3:
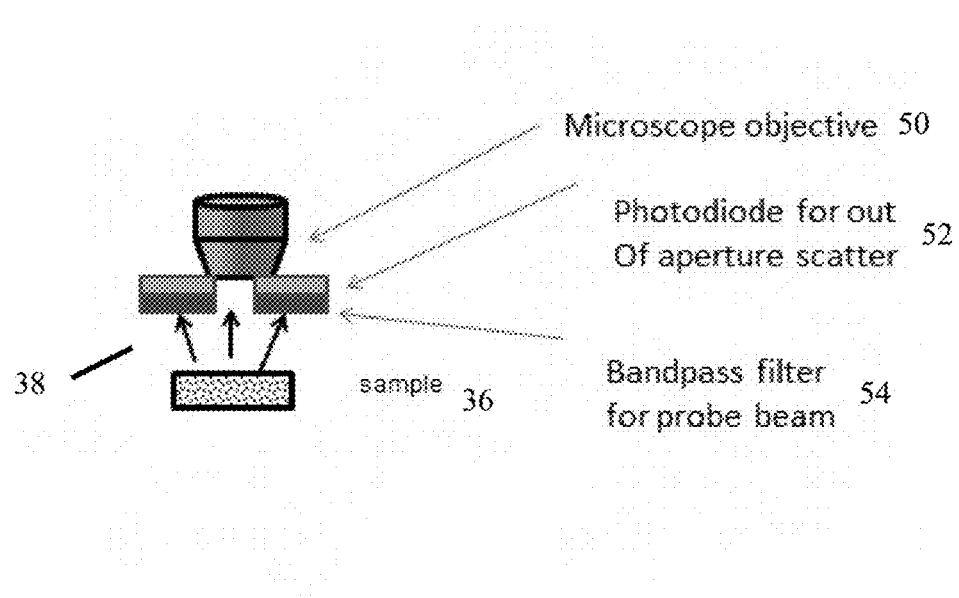
FIG. 3 is a block diagram of an example of a microscope aperture area used with the disclosed technology.

The stimulated fluorescent signal is shown as being collected in the backscatter (or epi) direction in FIG. 2, and FIG. 3. In some applications of MP-STEM imaging stimulated imaging and seFLIM imaging, such as in imaging tissue cultures or tissue sections, a signal can be collected in the forward scattered direction as shown in FIG. 2.

In FIG. 2, the stimulated signal can be collected by a detector 38 in the backscattered direction, either within the optical aperture of the system or by a large area annular photodiode around the microscope illumination aperture. For very deep tissue imaging using dipole backscattered emission, the signal is collected in the imaging aperture and with a confocal pinhole 40, in front of the collection aperture, as shown in FIG. 2. A large photo diode (diameter up to 1 cm) can be used to collect multiple backscattered forward stimulated emissions. An isolation optical filter 28, to remove pump light, can be placed in front of the lock-in amplifier 32 as shown in FIG. 2 for direct backscattered light. For multiple backscatter collection the optical filter can be placed in front of the microscope objective, as shown in FIG. 2 and FIG. 3. In FIG. 3, the microscope objective 50 collects light for single and multiple backscattered photons in multi-photon stimulated emission processes. The large photon diode SNR rapidly degrades for tissue imaging depth below wavelength dependent scattering length.

The time sequence of pump and probe beam signals are shown in FIG. 4. The imaging signal corresponds to the stimulated gain in intensity of the probe beam, computed as the difference between the probe signal from the fluorescent molecular excited state populated by the pump beam, and the un-excited molecular probe signal with the pump beam off. Standard interference filters can be used to separate pump and probe photons because they are separate in wavelength by >10 nm. The light is detected in the backward scattered direction by the "epi" light lock-in system. In some applications a standard non-lock-in system can be used in the epi direction. In some other applications the signal can be detected in the forward direction.

FIG. 5 provides a table of pump and probe wavelengths for 1, 2 3 and 4 photons for both excitation and stimulated emission in STEM and MP-STEM for proteins and DNA as well as two electron transport cofactors NADH and FAD, widely used in cellular metabolic imaging. For proteins and DNA, the single photon pump and probe wavelengths are in the deep UV and cannot be imaged efficiently, and usually without tissue damage in-vivo. With 2-photon excitation and emission MP-STEM imaging the wavelengths are moved into green and red, suitable for imaging with a depth of about 200 microns. Using 3-photon emission MP-STEM imaging, proteins and DNA can be imaged in near infrared, at depth of 300 microns or more.

The electron transport cofactors NADH and FAD can be imaged in the near IR with both 2 and 3 photon excitation and emission MP-STEM imaging. With 3 photon imaging, image depth approaching one millimeter can be achieved enabling in-vivo examination of tissue metabolism to a depth of up to 1 millimeter. A 4-photon excitation process for certain molecules move the excitation window far into the IR, where water absorption increases.

For depth in in-vivo MP-STEM imaging, the water windows at about 1300 nm and 1650-1850 nm can be used. Other wavelengths can be used but these are known regions of water transparency. In these wavelength ranges images down to 1 mm and more can be obtained. As shown in the Table in FIG. 5, MP-STEM imaging with 3 or 4 photons, from the pump and probe beams can be used for the electron transport cofactors. At longer wavelengths the backscattered photons can be collected at large angles outside of the microscope imaging objective taking advantage of the low tissue absorption at these wavelengths. The limit in IR wavelength is due to the increasing water absorption above about 1800 nm.

FIG. 6 shows the axial (along the optic axis of the microscope) and transverse (in the image plane of the microscope focus) Point Spread Functions (PSF) decrease in MP-STEM microscopes compared to standard STEM imaging. In this system the axial transverse point of the microscope system has a numerical aperture (NA) of 1.2 and a pump wavelength of 1080 nm and a probe wavelength of 1380 nm. Plotted are the PSFs for the probe beam, a STEM system, a 2 pse MP-STEM system, a 3 pse MP-STEM system and a 4 pse MP-STEM system. The PSF of the 3 pse system axial ½ width is about 50% of the probe wavelength enabling some dipole-like backscatter imaging. The PSF of the 4 pse system axial/width is about 28% of the probe wavelength enabling more dipole-like backscatter.

Figure 6A:
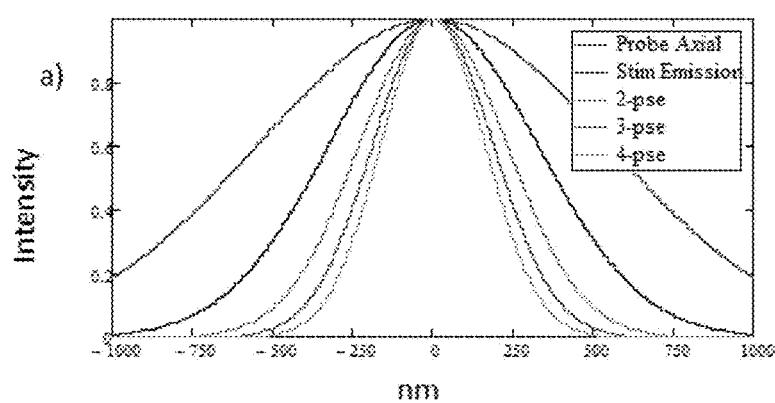
FIG. 6a is a graphical depiction of Point Spread Functions of probe beam (PSF) in an axial direction for 1 pse (2 photons), 2 pse (4 photons) and 3 pse (6 photons) imaging.
Figure 6B:
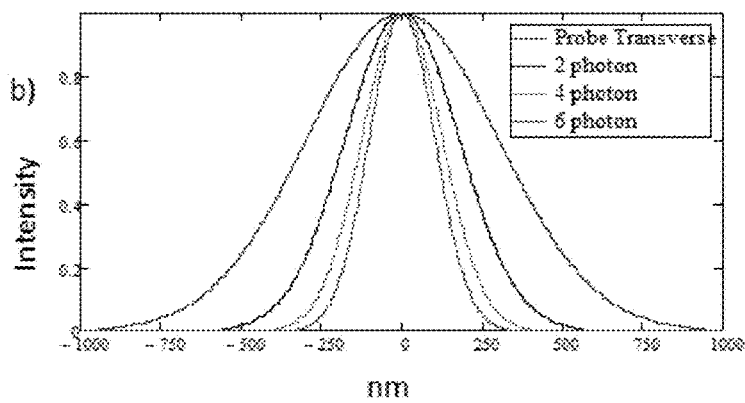
FIG. 6b is a graphical depiction of Point Spread Functions of probe beam (PSF) in transverse direction for 2 photon (1 pse), 4 photons (2 pse) and 6 photons (3 pse) systems.
Figure 7:
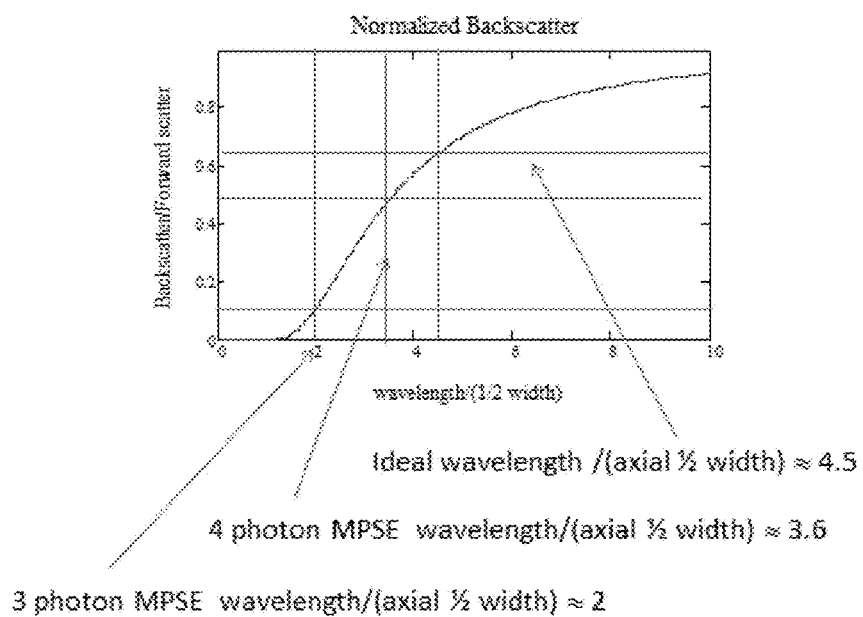
FIG. 7 is a graphical depiction of a ratio of back scattered to forward scattered stimulated emission as a function ratio of emission wavelength to emission axial ½ width.

FIG. 7 plots the ratio of the forward to backscattered gain for a Gaussian distribution of excited states along the optic axis as a function of the ratio of stimulating wavelength $\lambda_{pr}$ to Gaussian ½ width ($\lambda_{pr}/w$). For a $\lambda_{pr}/w>8$ the backscatter gain approaches the forward gain, while for $\lambda_{pr}/w<1.5$ the backscatter approaches zero. For a volume emitter the optimum signal is achieved for a $\lambda_{pr}/w\approx4$-5. For larger $\lambda_{pr}/w$ ratios, the emission spot is small, reducing the number of emitters in a uniform volume of emitters. As the emission spot increases in size so does the number of emitters. Standard STEM systems produce little backward gain. The 2 spe system which has a $\lambda_{pr}/w\approx1.5$, produces a stimulated emission that can be too small to measure. In the 3 spe system microscope system parameters defined above in FIG. 6, $\lambda_{pr}/w\approx2$, and produces measurable backscattered stimulated emission. A 4 pse system would produce $\lambda_{pr}/w\approx3.6$, close to an optimized backscatter/forward-scatter ratio.

In the implementations and methods disclosed here, the use of MP-STEM imaging can determine the molecular fluorescent lifetime by measuring the signal with two or more temporal delays between the pump and probe laser pulses as shown in FIG. 9. Two different time delay measurements can be used to measure the molecular concentrations with a single decay constant. This process is called stimulated emission Fluorescent Lifetime Microscopy (seFLIM).

In FIG. 11, the difference in arrival time between the pulses is marked at 0.4, 300, 1000 and 3000 picoseconds. These delays are useful in measuring bound and free NADH and NADPH concentrations in metabolic imaging of cells. Four measurements can be used to model a 2 component multiple exponential decay, while six measurements can model a three component decay curve, when the decay constants are unknown. If there are constraints on lifetime and number of components in the fluorescent decay curve, as in the case of NADH, fewer time delay measurement points can be required. Thus by using the technique of seFLIM, the concentration of free and bound molecules can be rapidly determined.

Stimulated Fluorescent and MP-STEM Microscope Theory

The absorption cross section, $\sigma_{abs}$, for optical radiation for a single chromophore at room temperature is about $10^{-6}$ $cm^2$. In a tightly focused laser beam with a beam waist, S ($\sim 10^9$ cm$^2$) the integrated intensity attenuation of the excitation pump beam $\Delta I_{pu}/I_{pu}$ is proportional to the ratio between $\sigma_{abs}$ and S, where $I_{pu}$ is the intensity in the excitation pump beam as shown in Eq. 1:

$$\Delta I_{pu}/I_{pu} = -N_0 \sigma_{abs}/S \quad (1)$$

$N_0$ is the number of molecules in the ground state. For a single chromophore, $\Delta I_{pu}/I_{pu}$ is of the order of $10^{-7}$. The stimulated emission cross section, $\sigma_{stim}$, is comparable to the $\sigma_{abs}$, and the change in intensity of a stimulated probe beam $I_{pr}$ is:

$$\Delta I_{pr}/I_{pr} = -N_2 \sigma_{stim}/S \quad (2)$$

$N_2$ is the small number of molecules transiently probed by the stimulating probe beam. For a single chromophore $\Delta I_{pr}/I_{pr} = 10^{-7}$.

Normally, SEM is conducted in a non-saturating condition of the four-level system (FIG. 1a). Under this condition, $N_2$ in equation (2) originates from a linear excitation: $N_2 \propto N_0 I_{pu} \sigma_{abs[0 \to 1]}/S$. This relation, together with equation (1), indicates that the final signal $\Delta I_{pr}$ is linearly dependent on both $I_{pu}$ and $I_{pr}$:

$$\Delta I_{pr} \propto N_0 I_{pu} I_{pr} (\sigma_{abs[0 \to 1]}/S)/(\sigma_{stim[2 \to 3]}/S) \quad (3)$$

The MPE and MP-STEM each require two or more photons to interact simultaneously with the fluorescent molecules. However, in MP-STEM the two processes of excitation and stimulated emission can be separated in time by 0.3-4000 ps, and thus can initially be considered to be independent. The time scale of the "simultaneous" arrival of the photons is determined by the intermediate virtual lifetime $\Delta\tau \approx 10^{-16}$ s (as per the uncertainty principle). Hence, a 2-photon cross section ($\sigma_2$) is about $10^{-49}$ cm$^4$ (s/photon) (or $A^2 \Delta\tau$), a 3-photon cross section ($\sigma_3$) is about $10^{-82}$ cm$^6$ (s/photon)$^2$ (or $A^3 \Delta\tau^2$) and a 4-photon process is about $10^{-115}$ cm$^{10}$ (s/photon)$^3$ (or $A^4 \Delta\tau^3$). These small cross sections require significantly higher incident laser focal intensities, and shorter pulses in MP-STEM than single photon SEM. Pulses of less than 100 fs/pulse are often used. This is true for both the pump and probe beams.

Only one MP-STEM emission process/molecule/pulse can occur. Therefore the pump pulse can operate very close to saturation at focus of the transition to achieve the maximum population in the excited state, and to increase the probability of the stimulated emission pulse to de-excite pumped molecules. In saturation about 40-50% of the molecules at focus can be transferred to the excited state during the 100 fs excitation pulse, thus $N_2 \approx N_0/2$, and:

$$\Delta I_{pr} \propto N_0 I_{pr}/2 (\sigma_{stim[2 \to 3]}/S) \quad (4)$$

An n-photon excitation or emission process is proportional to $\sigma_n I_{peak}^n \tau$, where $I_{pk}^n$ is the pump or probe peak intensity, $\sigma_n$ is the n photon cross section, and $\tau$ is the pulse length. For a square pulse in time at saturation: $\sigma_n I_{peak}^n \tau = 1$. Therefore, the saturation peak intensity for the pump beam is:

$$I_{pks}^n \approx (\sigma_n \tau)^{-1/n} \quad (5)$$

The probe beam can operate at the high end of the linear gain curve to enable computation of molecular concentrations that require a linear relationship of the gain and the concentration. This occurs at about 50-60% of saturation.

Using diffraction limited focusing geometry, the relation between the average incident photon flux ($P_{avg}$, in units of photons/s) and $I_{peak}$ is:

$$P_{avg} \approx (0.61)^2 \lambda^2 (f \cdot \tau) I_{peak}/(NA)^2 \quad (6)$$

where f is the pulse repetition rate. Combing Eq. 6 and the saturation power for the n photo process ($P_{avg}^{ns}$) can be estimated as:

$$P_{avg}^{ns} \approx (0.61)^2 \lambda^2 (f \cdot \tau) \cdot (\sigma_n \tau)^{-\frac{1}{n}} / (NA^2) \quad (7)$$

The maximum intensity at focus in practice is limited by optical breakdown of the tissue and is wavelength dependent. The pulsed optical damage threshold measured for photon wavelengths above 1 μm for 100 fsec pulses has been shown to be about $2 \times 10^{14}$ W/cm$^2$, or about 20 nJ/μm$^2$/(100 fs pulse). Below 1 μm wavelength the damage threshold increases. With a high NA (1.3) objective lens and 100-fs pulses at 80-MHz repetition rate and 1.0 um excitation wavelength, the estimated saturation powers for one, two, three, and four-photon processes are, respectively, ≈0.3 mW (0.1 nJ/pulse), ≈30 mW (1 nJ/pulse), ≈150 mW (5 nJ/pulse), and ≈300 mW (10 nJ/pulse) by Eq. 8 and the excitation cross sections estimated above. Thus in the limit the damage threshold for 2 pse and 3 spse is more limited by average power of the pump and probe beams than the damage threshold for 70-100 fs NIR pulses.

The laser power used will have to be significantly increased for imaging at 1-3 absorption/scattering depths. At 800 nm, the absorption depth in tissue is 120 μm, at 1000 nm wavelength the absorption depth in brain tissue is ~200 μm, and at 1300 nm the absorption depth is 300 μm. Therefore it is advantaged to operate above 1 micron in pump wavelength. MP-STEM can operate at about 0-3 absorption depths (15% transmission to focus for the pump wavelength). Thus the maximum incident estimated laser power for two and three-photon processes are, respectively, ≈600 mW (20 nJ/pulse) and ≈3000 mW (100 nJ/pulse) at the surface. These average powers are high. It is sometimes better to operate at a reduced laser rep rate of 10 MHz. Reducing the laser repetition rate can have an effect on the lock-in photon detection protocol, which will be discussed below.

The Point Spread Function of a MP-STEM system (PSF$_{MP-STEM}$) scales as the single photon illumination Point Spread Function (PSF$_{il}$) to the power equal to the number of photons in the process. The pump PSF (PSF$_{pu}$) and probe PSF (PSF$_{pr}$) are each raised to the power of the number of photons used per each electronic transition, n, and are multiplied together to produce the PSF$_{MP-STEM}$ as shown in Eq 8.

$$(PSF_{MP-STEM}) = (PSF_{pu})^n \cdot (PSF_{pu})^n \quad (8)$$

FIGS. 6a-b show the PSFs in both the axial and transverse direction for the probe beam, the standard STEM probe stimulated emission spot as well as the 2 pse, 3 pse and 4 pse MP-STEM stimulated emission spots, for a 1.2 NA objective, pump wavelength of 1020 nm and a probe wavelength of 1380 nm. These wavelengths are useful for 3 pse from NADH and are used throughout the examples given below.

In the 4 pse process the ½ point intensity point of the PSF in the axial direction (PSF$_{axial}$) is about 40% of the probe wavelength, 3 pse process the ½ point intensity point PSF$_{axial}$ is about 50% of the probe wavelength and the 2 photon process ½ point intensity point is about 62% of the wavelength. These differences in ½ width result in a difference in direct stimulated emission backscatter as discussed below in reference to FIG. 7. As shown in FIGS. 6a-b, in the transverse plane, the ½ width of the 3 pse PSF is 240 nm and, in the axial direction, the ½ width is the 3 pse is 700 nm.

It is known that a single fluorophore will emit stimulated emission into the backward illumination and forward propagating modes into the stimulating mode with equal probability. The fluorophore is small relative to the optical wavelength and cannot tell the direction of propagation of the field. However, as the stimulated emission gain length increases the backscatter decreases. Although the gain in the stimulated field is small in microscopy because of the small focal spot, as the probe beam propagates along the forward direction through the focal spot the stimulated emission photons add in phase, increasing the coherent traveling field. The stimulated emission in the backpropagation direction adds out of phase as the incident beam propagates forward. Thus as the gain medium length increases, the backscattered stimulated emission photons from axially spatially separate fluorophores destructively interfere. The backscatter stimulated field quickly decreases over sub-wavelength dimensions. This small sample coherent backscatter is related to the small structure backscatter in Coherent Anti-Stocks Raman Scattering.

The forward and backscattered fields generated along the optic axis can be modeled over the focal spot of length $2Z_1$ by the following equation:

$$G_{(f,b)}(t) = \int_{-z_1}^{z_1} C(z) E_{pr} Re\{e^{-i(kx + w_{pr}t + \theta(z))}\} PSF_{axial}(z) dz \quad (9)$$

$G_f$ is the forward far field electric field gain, and $G_b$ backward far field electric field gain. $E_{pr}$ is the probe electric field, $\omega_{pr}$ is the probe frequency, $k$ is the propagation constant and $\theta(z)$ is the phase of the emitted photons at each point. $C(z)$ is the gain factor that depends on the local concentration of fluorophores and stimulated emission cross section. It is assumed that in the forward direction $\theta(z)=0$ for all points, as the stimulated photons add in phase. In the backward propagating direction $\theta(z)$ is different at each point as the there is a time change for the emission of each axial point. It assumes that $z=0$ is at the center of the $PSF_{axial}(z)$, and at that point $\theta(z)=0$.

FIG. 7 plots the ratio of the forward to backscattered electric field gain ($G_f/G_b$) for a Gaussian distribution of excited states along the optic axis as a function of the ratio of stimulating wavelength $\lambda_{pr}$ to Gaussian ½ width, w, that is ($\lambda_{pr}/w$). For $\lambda_{pr}/w > 8$ the backscatter gain approaches the forward gain, while for $\lambda_{pr}/w < 1.5$ the backscatter approaches zero. The total Gain is thus $G_f + G_b$, when $\lambda_{pr}/w > 8$, $G_f = G_b$.

Figure 8:
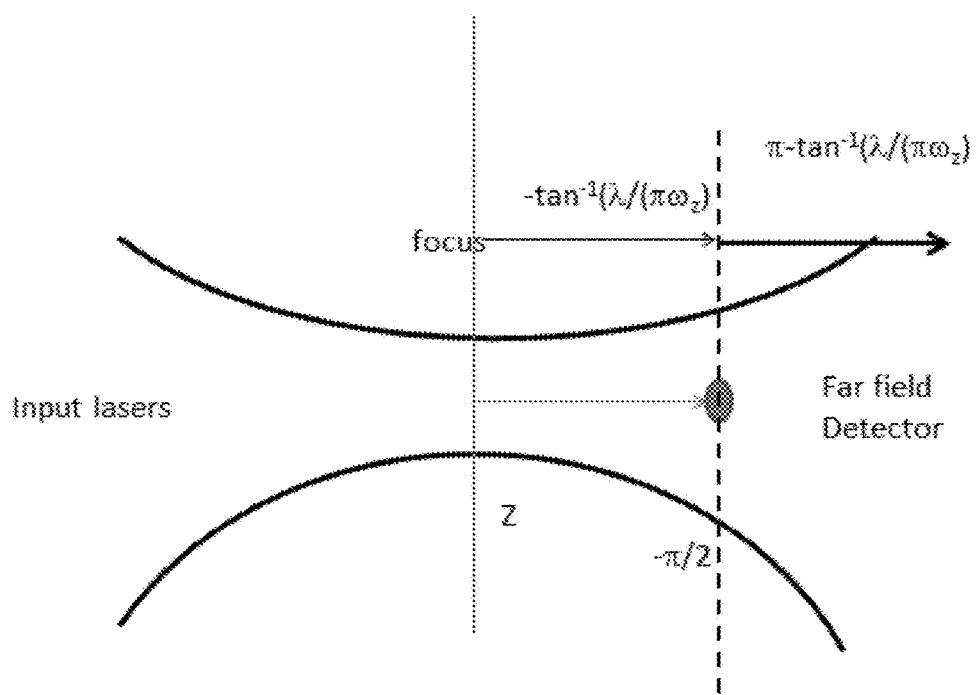
FIG. 8 is an illustration of a direction of the stimulated emission in normal sized focal spots and MP-STEM spots reduced to <70% of the probe wavelength in the axial direction.

For a uniform volume of emitters the optimum signal is achieved for a $\lambda_{pr}/w \approx 4\text{-}5$. For larger $\lambda_{pr}/w$ ratios, the emission spot is small and the number of emitters present produces weak stimulated emission. The 2 spe system produces a stimulated emission backscatter that can be too small to measure. In the 3 spe system microscope designed for NADH fluorescence $\lambda_{pr}/w \approx 2$, which produces $G_f/G_g \approx 0.1$ backscattered stimulated emission. The 4 pse system produces a $\lambda_{pr}/w \approx 3.1$ ($G_f/G_b \approx 0.5$). For a microscope objective of NA=1.4 for the 3 spe microscope system (for in-vitro imaging), then $\lambda_{pr}/w \approx 3.1$ ($G_f/G_g \approx 0.4$) which is close to the ratio for peak emission. Below a method to further reduce the focal spot axial length in MP-STEM is discussed. In the forward direction the bright field background noise is primarily from photons in the stimulating probe beam and the accompanying photon noise statistics. This is also the case for collection of multiply scattered epi collected signals. For backward propagating dipole emission from a small focal volume in a confocal microscope the background noise comprises backscattered probe photons from refractive index (RI) gradients in the focal volume and multiple backscattered photons back into the confocal aperture. RI noise is at most about $5 \times 10^{-4}$ of the incident beam, at the interface of cytoplasm and cell nuclei. Thus backscatter noise is substantially less than forward and multiple backscatter noise. The signals from forward scatter large focal spots and forward and backscattered 3 pse and 4 pse focal spots are summarized in FIG. 8.

Dipole-like scattering is particularly important in deep tissue imaging. This enables much more signal light and fewer background photons to be collected in the illumination aperture of the microscope. In addition it provides a confocal scattering image of the tissue understudy, enabling at least two forms of imaging with each image scan.

There are certain advantages of a 3 and 4 photon stimulation emission process (3 pse and 4 pse), compared to a 2 photon stimulated emission process (2 pse).

1) The laser wavelengths are generally longer in 3 pse and 4 pse processes enabling deeper tissue penetration into the tissue and less backscatter loss.

2) The higher damage threshold of the tissue at longer wavelength allows the system to operate as close to saturation as does a 2 pse process.

3) There is less multiphoton excitation near the surface in 3 pse than 2 pse because of the lower absorption and emission cross sections. Thus since the out of focus processes are not in saturation, and depend on the product of the excited state populations, the probability of emission from 3 pse is lower than for 2 pse.

4) The focal spot (in both the transverse and axial dimensions) for 3 and 4 pse are smaller percentage of the probe wavelength than 2 pse. A smaller focal spot enables more dipole-like focal stimulated emission.

5) In 3 and 4 pse processes the primary photons are of lower energy and scale into the IR region of the spectrum. Wavelengths from 1000-1800 nm are achievable with femtosecond fiber lasers, which are significantly smaller and less expensive than solid state lasers, such as Ti: Sapphire lasers often used in multiphoton microscopy.

The detection of a change of pump intensity of $\Delta I_{pr}/I_{pr} \approx 10^{-7}/$molecule requires sensitivity detection. The best detection is achieved with low bandwidth phase sensitive lock-in techniques. A $\Delta I_{pr}/I_{pr} \approx 10^{-7}$ has been achieved in measuring to be 60 nM of crystal violet with a signal-to-noise ratio of 1:1 with a 1 second lock-in integration time. To achieve this level of detection a close to photon shot noise limit Ti:Sapphire laser source that is at >1 MHz repetition rate is used. The photon noise in a hot noise limited probe laser is $I_{pr}^{1/2}$, where the probe intensity is $I_{pr}$. For rapid scanning of <200 μsec/pixel of $\Delta I_{pr}/I_{pr} \approx 10^{-4}\text{-}10^{-5}$ has been achieved.

One can calculate the sensitivity, and the required pixel dwell time for a high speed MP-STEM system. The largest signals are achieved for pumping at saturation, and stimulated emission probe at near 60% of saturation. At pump saturation 50% of the molecules at focus will be in the lowest excited state after decay from the upper pumped level. With 100 fs pump pulses we assume no decay out of the pumped levels during the pulse. The maximum photopumped population is 50% given the equivalence of the Einstein emission and absorption coefficients. However in the probe beam, it is desirable to provide stimulated emission gain that is in the linear range to provide an accurate measure of the concentration of emitters. At incident intensity 20% above gain saturation the stimulated emission gain is significantly reduced and can approach zero. Again because the probe pulse is about 100 fs there is minimal decay from the upper and lower excited states during the probe pulse and about 50% of the molecules will be in each the upper and lower level of the transition. Thus the probe intensity can be below the stimulated emission saturation intensity, e.g., the probe beam intensity can be about 60% of fluorescent saturation, in order to maintain linearity of probe gain.

In one example, a 20 second frame time was used for a 500×500 pixel image, or a pixel dwell time of 80 μsec for a 3 spe system designed to detect NADH at a 20 MHz laser pulse repletion rate, and a 2 MHz sample window (~10 pulses/sample window) in the ≈200 mW (2.0 nJ/pulse) 1000 nm pump region and ≈120 mW (1.2 nJ/pulse, $8.6×10^9$ photons/pulse) 1380 nm probe region. These are appropriate numbers for high frame rate forward collection and multiple scatter back collection. For dipole scattering in the epi direction, lower powers and repetition rates can be used. The power at the surface varies from the focal power numbers to about 10 times higher depending on the focal depth.

The pump power is in saturation and the probe power is at the high end of the linear gain region. For the probe at 20 MHz laser repetition rate about $2.2×10^{13}$ photons in 1600 pulses are delivered per pixel/(80 μs dwell time). Half of the probe pulses are delivered with the pump pulse off. In the 800 pulses with both probe and pump on, each molecule can be excited at most 400 times (once per pulse) if the pump power drives molecular transitions into saturation. The photon probe shot noise in this time frame is about $4.7×10^6$ photons. The signal is in the linear part of the probe gain curve, and thus about 400×n gain photons/molecule can be added to the probe gain/pixel dwell time.

In a multiphoton stimulated emission transition n photons can be added to the probe beam for each multiphoton transition, where n=1, 2, 3, or 4. Thus a three photon stimulated transition require about $3.9×10^3$ molecules/pixel to achieve an SNR=1:1. Then of a clean signal with a SNR=5:1 requires ~$1.9×10^4$ molecules/pixel. The emitter volume is significantly smaller than the probe volume. For the system parameters in FIG. 9, the ½ width of the focal ellipsoid is ~0.02 μm³, and the required emitter concentration for high SNR rapid scanning is 2.5 mM. This is comparable to the concentration of NADH in cells. In mitochondria, the concentration of NADH is higher.

For high NA=1.2 MP-STEM microscopic foci, and isolated fluorophores that produce dipole backscattered fields, there is less background photon noise. In the backscatter direction there are two major contributions to the background noise.

1) The tissue refractive index gradient backscattering. In cells, the refractive index change between the cytoplasm and nucleus is about 4% which results in a local backscatter of the incident beam [13] of $3×10^{-4}$ of the incident field.

2) Multiple backscattered probe photons that come through the focal point defining pinhole in the collection aperture. In the backscattered direction the refractive index gradient at the cellular nuclei can produce, about, $6×10^9$ photons, with shot noise limit of $7.7×10^4$.

A pure dipole emitter will emit half the photons in the backward direction. In the example above the ½ width is about 50% of $\lambda_{pr}$ and backscatter is ~10% of the forward scatter. Thus using the forward scatter photon number calculated above for an SNR=5 in the forward direction, about $1.5×10^6$ photons are backscattered, while the noise is about $9.1×10^4$, for a photon SNR of 16. A total system SNR of ~$10^4$ is required. Thus for rapid scanning, a lock-in may not be required. With a lock-in amplifier backscatter detection will detect a smaller number of emitters than forward scattered detection. Thus the scan rate can be increased. In addition, it is possible not to use lock-in techniques but rather standard low noise electronic detection. In many pixels the background index gradient scatter can be much reduced making a detectable signal limit much smaller.

Standard wide field fluorescent imaging can be useful for detecting very low concentrations of fluorescent molecules, while scanning fluorescing imaging is useful for detecting moderate concentrations of highly fluorescent molecules at depth in tissues. Scanning STEM imaging is most useful for superficially placed weakly fluorescent molecules. MP-STEM imaging is useful for detecting deep weak and moderately fluorescent molecules present in moderate to high concentrations. In addition MP-STEM imaging is useful for frequency shifting the UV fluorescence of weakly fluorescent molecules into the green or red to enable imaging molecules that would not emit radiation through tissue.

MP-STEM signals can be recorded in the far field of a high NA microscope system, taking into consideration the far field phase relationship between the probe beam with the signal gain field, the T radian probe Gouy phase change thru focus and the position of the emitter relative to the microscope focal plane.

In stimulated coherent spectroscopy, the detected signal can be described in terms of classical wave interference in the far field. The induced signal field $E_s$ of frequency $\omega_s$, is generated at point r through a nonlinear process and is detected at a far-field point R. At the detection point, the induced field is mixed with a local oscillator field $E_{LO}(R)$, which is phase coherent with the former. The total intensity at the far field detector is then written as:

$$S(R) = \left(\frac{n(\omega_s)c}{8\pi}\right)|E_s(R) + E_{LO}(R)|^2 = I_s(R) + I_{LO}(R) + \frac{2n(\omega_s)c}{8\pi}\operatorname{Re}\{E_s(R) \cdot E_{LO}^*(R)\}$$

where $n(\omega_s)$ is the refractive index of the material at frequency $\omega_s$, c is the speed of light, and $I_s$, $I_{LO}$ are the intensities of the induced signal and the local oscillator fields, respectively.

The fields E(R) are complex with a given wave vector that depends parametrically on R. The heterodyne contribution to the signal through which stimulated coherent optical signals can be understood is shown in Eq. 10

$$S_{het}(R) = \frac{2n(\omega_s)c}{8\pi}\operatorname{Re}\{E_s(R) \cdot E_{LO}^*(R)\} \tag{10}$$

The excitation field provides the local oscillator that interferes with the signal field in the far field.

Coherent stimulated multiphoton processes can be analyzed in terms of the third, or higher, order molecular susceptibility. MP-STEM is different from SRS because the pump beam does not coherently participate in the multiphoton stimulated emission process. The Kasha decay from the pumped excited band into the lowest excited state and the variable delay between the pump and probe pulses causes a loss of coherence between excitation and stimulated emission processes. However, the pump does contribute to the process by creating the population of excited states that participate in stimulated emission.

In forward scattered MP-STEM the signal of interest is the probe gain field $G_{pr}(r)$ or the signal field $E_{si}(r)$, which depends upon the induced polarization, $P_{pr}^n(\omega_{pr}, r)$, generated at focus, where n is the number of emitted probe photons per event, and is described by Eq. 11, $$P_{pr}^n(\omega_{pr},r) \propto |E_{pr}(r)|^{2n-2} \cdot E_{pr}(r) \cdot I_{pu}^n(r) \cdot e^{-\Delta t/\tau} \cdot \chi^{2n-1}(\omega_{pr},r) \quad (11)$$

Here $\chi^{2n-1}(\omega_{pr}, r)$ is the molecular susceptibility of the medium for the relevant order of susceptibility. $E_{pr}$ is the probe electric field, $I_{pu}$ is the pump intensity, and $\Delta t$ is the delay between the peak of the pump pulse and the peak of the probe pulse, $\tau$ is the excited state decay constant.

In 2 photon excitation and stimulated emission processes a third order susceptibility is used, while in 3 photon excitation and stimulated processes a fifth order susceptibility is require.

The induced electric field $E_{si}$ generated at point r near focus is detected at a far field point R where it is mixed with a local oscillator field that is phase coherent with the induced field. In the forward direction the local oscillator field is $E_{pr}$, while in the backscatter direction the local oscillator field is the index gradient backscatter field $E_{bs}$ as shown in FIG. 7. A spatial phase shift for the measured field at a detection point R relative to the phase at the excitation point r can occur, which depends on the excitation and detection geometry. For forward scatter it is assumed that $\phi$ is the spatial phase of the induced field at R relative to the phase at the origination point r, and $\alpha$ measures a similar spatial phase shift between r and R for the probe local oscillator field. These relations are shown in Eq. 12 and Eq. 13

$$E_s(R) \approx P_n(\omega_{pr},r) e^{-i\phi} \quad (12)$$

$$E_{LO}(R) \approx E_{pr}(r) e^{-i\alpha} \quad (13)$$

The stimulated field in a MP-STEM microscope be using Eq. 12 and Eq. 13;

$$E_s(R) = P_{pr}^n(\omega_{pr},r) \propto |E_{pr}(r)|^{2(n-1)} \cdot E_{pr}(r) \cdot I_{pu}^n(r) \cdot e^{-\Delta t/\tau} \cdot \chi^{2n-1}(\omega_{pr},r) \cdot e^{-i\phi} \quad (14)$$

When the stimulated emission from a plane of dipoles perpendicular to the direction of field propagation, is measured in the far field, there is $\phi=-\pi/2$ radian change in the phase between the dipole emission plane and the far field. When a single dipole is present at focus, the induced field exhibits a phase that is spatially invariant, i.e., $\phi=0$.

In a MP-STEM microscope the scattering volume can be treated as a dipole, as it is less than a wavelength in the transverse dimensions. Therefore in the far field, $\phi=0$. Thus the heterodyne term in the forward far field for a dipole at focus is shown in Eq. 15

$$S_{pr}^n(\omega_{pr},R) \propto [I_{pu}(r)]^n \cdot e^{-\Delta t/\tau} |E_{pr}(r)|^{2(n-1)} Re\{E_{pr}(r) \cdot E_{pr}^*(R) \cdot \chi^{2n-1}(\omega_{pr},r)\} \quad (15)$$

This relation contains the term $E_{pr}(r) \cdot E_{pr}^*(R)$ which carries phase information that depends solely on the spatial profile of the excitation field. Using Eq. 13, this latter term can be rewritten as $|E_{pr}(r)|^2 e^{i\alpha}$. The Gouy phase shift in a high NA microscope system from the focus to the far field is $\alpha=\pi/2$. We can thus write:

$$S_{pr}^n(\omega_{pr}, R) \propto [I_{pr}(r)]^n \cdot [I_{pu}(r)]^n \cdot e^{-\frac{\Delta t}{\tau}} \cdot Im\{\chi^{2n-1}(\omega_{pr},r)\} \quad (16)$$

Eq. 16 describes the forward scattered gain in MP-STEM heterodyne signal with the small scatterer volume centered on the focal plane.

In MP-STEM backscatter signal detection, the local oscillator signal, when it is present, comes from probe beam reflection from refractive index field gradients and nanoparticles within the probe beam focus. The backscatter source can be anywhere within the single photon focus of the microscope, or the acceptance confocal pinhole aperture. Therefore, the effect of the Guoy phase, and focal position of the backscatter source and its interference with the MP-STEM signal can be considered. In deriving the backscatter field phase relative to the stimulated emission field we will follow the approach of Hwang and Moerner for nanoparticle scattering.

A nanoparticle can be modeled has having a real and imaginary scattering amplitude $\alpha/A+i\varphi$ where $\alpha/a$ is the real part responsible for absorption and $\varphi$ is the phase change associated with the transmission of a laser beam. After the nanoparticle, the probe field (with $e^{-i\omega t}$ assumed) is $$E_r(r) = E_{pr}(r) + E_{sc}(r) = E_{pr}(e^{ikr}) + \left(\frac{\sigma}{A}\right)E_{pr}(e^{ikr}) + i\varphi E_{pr}(e^{ikr}) \quad (17)$$

In the backscattered direction, the phase and refractive index gradient dependent scatter $E_{bsRI}(r)$ is of significance. Incorporating the phase of the induced backscatter, $\varphi_{sc}(z)$, $E_{bsRI}(r)$ is:

$$E_{bsRI}(r) \propto i\varphi E_{pr}(ikr+i\varphi_{sc}(r)) \quad (18)$$

This field interferes with the stimulated backscatter $E_{bsSE}(r)$. In order to calculate the far field signal, the contributions of the Gouy phase and the scatterer induced phase can be taken into account.

The Gouy phase shift of a 2 dimensional wavefront in a high NA microscope is a total of $\pi$ radians. The phase of the probe beam is described in FIG. 11. Near focus, at the distance z (z is positive for an advance in the propagation direction) on axis, the phase shift is given by $-\tan^{-1}(z/z_R)$, where $\omega_0$ is the beam radius at the focus (waist). The quantity $z_R$ is equal to $\pi\omega_0/\lambda_{pr}$, the Rayleigh range of the waist. This phase shift approaches a constant value of $\pi/2$ between the focal position and a large distance in the far field.

A forward scattered beam from a nanoparticle has a phase shift of $\pi/2$ radians both in the far-field and the near-field. That is, when a field is present at the input of a sub-wavelength aperture the phase change through the aperture is $-\pi/2$. Using Babinet's principle, when the complimentary point scatterer (absorber, or refractive index gradient) is present, in place of the aperture, the scattered beam undergoes a phase change of $+\pi/2$ radians. Thus in the far field $\varphi(R)$ is:

$$\varphi(R) = \pi - \tan^{-1}\left(\frac{r}{r_R}\right) \quad (19)$$

The far field in the backscatter direction $E_{bs}$ is the sum of the backscatter refractive index gradient phase change particle scatter, $E_{bsRI}$, and the backscattered stimulated emission $E_{bsSE}$.

$$E_{bs}(R) = E_{bsRI}(R) + E_{bsSE}(R) \quad (20)$$

The backscattered intensity is $$I_{bs}(R) \propto I_{bsRI}(R) + I_{bsSE}(R) + Re\{E_{bsSE}(R) \cdot E_{bsRI}^*(R)\} \quad (21)$$

The dipole induced backscatter is assumed to originate from the plane of focus, while the index gradient backscatter can originate anyplace near focus. Therefore the contribution of a variable Gouy phase is mostly contributed by the RI induced scatter. Secondly in the backscatter direction the stimulated emission experiences a 0 phase shift as it propagates in the backward direction. We also assume since the n photon process is phase matched and resonant, such that the $re\{\chi^{2n-1}(\omega_{pr},r)\}=0$. Therefore using Eq. 20 and Eq. 21 the heterodyne backscatter term $S_{bs}(R)$ is:

$$S_{bsv}(R) \propto \left[[I_{pr}(r)]^{n-1} \cdot [I_{pu}(r)]^n \cdot I_{bsRI}^{\frac{1}{2}}(r) \cdot I_{bsRI}^{\frac{1}{2}}(r) \cdot e^{-\frac{\Delta t}{\tau}} \cdot \text{Im} \right. \quad (22)$$

$$\left. \{\chi^{2n-1}(\omega_{pr},r)\}\right]\left[1 - 2\varphi\sin\left(\tan^{-1}\left(\frac{z}{z_R}\right)\right)\right]$$

The backscatter from each pixel can have refractive index backscatter, stimulated emission backscatter or both. During the pulse train the presence or absence of back scatter can be determined by measuring the backscatter signal from pulses when the pump pulse is off. The position with the focus can be determined by interference of the backscatter with the pump off with a reference beam that can be used to focus the system. Many such approaches exist.

MP-STEM Signal Sensitivity and SNR

Large MP-STEM probe gain signals can be achieved when pumping at saturation. With 100 fs pump pulses, it is assumed there is no decay out of the excited state manifold in first 500 fs after the pulse. The maximum signals, for all fluorescent lifetimes, are achieved with a probe delay. $\Delta\tau_{pr}$, of about 0.5-1.0 ps.

The maximum photo-pumped population is 50% of the molecules at focus given the equivalence of the Einstein emission and absorption coefficients. It is desirable to provide stimulated emission gain that is in the linear range to provide an accurate measure of the concentration of emitters. Therefore, the probe beam intensity may not produce saturation, but about 50% of fluorescent saturation.

The goal of this calculation is to find the number of molecules at focus required to achieve a 60 second frame time for a 500×500 pixel image, with a pixel dwell time of 240 μsec. The system is designed as a 3 pse system to detect NAD(P)H. The pulse trains of the pump and probe pulses are shown in FIG. 2, as is a schematic of a MP-STEM system. A lock-in detection system can be used because of the small bright field gain signal relative to the forward propagating probe beam. A 10 MHz laser pulse repetition rate with a 80 fs pulse width, and a 1 MHz sample window (~10 pulses/sample window) can also be used. The power focus is ≈40 mW (4.0 nJ/pulse) in 1000 nm pump beam and ≈20 mW (2.0 nJ/pulse, $1.4\times10^{10}$ photons/pulse) 1380 nm probe beam with an NA=1.2. The power at the surface varies from the focal power numbers to 20 times higher depending on the focal depth.

It can be clear from the axial and transverse PSF's of MP-STEM system shown in FIG. 6 that a reduction of the emission spot volume occurs. Therefore, many input probe photons do not contribute to the gain signal. For the 3 pse system, the emission volume is ~4% of the probe spot on target. Therefore the efficiency of probe gain generation is smaller than a STEM system illuminating standard focal volume.

For the probe at 10 MHz laser repetition rate about $3.6\times10^{13}$ probe photons in 2400 pulses are delivered to focus/(240 μs dwell time). Half of the probe pulses are delivered with the pump pulse off. Thus about $0.6\times10^{12}$ photons contribute to probe gain focal volume in a 3 pse system. If the pump power drives molecular transitions into saturation then, in the 1200 pulses with both probe and pump on, each molecule in the emission volume can be excited at most 600 times (once per pulse with a 50% probability). In the limit the photon shot noise is the square root of the number of photons used. Thus the probe beam shot noise, with pump on, in the forward scattered direction is about $6.0\times10^6$ photons. The signal is in the linear part of the probe gain curve (~25% stimulated emission), and thus at most ~150×n gain photons/molecule can be added to the probe gain/pixel/(dwell time).

In a multiphoton stimulated emission transition, n photons are added to the probe beam for each multiphoton transition, where n=1, 2, 3, or 4. Thus in a 3 pse focal volume requires $1.3\times10^4$ molecules/focal volume to achieve an SNR=1:1. Then a signal with a SNR=3:1 requires ~$4.2\times10^4$ molecules/focal volume. For the system parameters in FIG. 6, the ½ width of the focal ellipsoid ½ width volume is ~0.0098 μm$^3$, and the required emitter concentration for high SNR rapid scanning is ~7.0 mM in the forward direction. This is larger than the concentration of most molecules in solution in living tissues. This means the pixel scan rate can be reduced to improve the signal detection, using more photons/pixel or the signal can be averaged over multiple pixels. The requirement for high spatial resolution for diffuse scatterers is unlikely unless there is a specific boundary near the resolution limit of the scan, such as in mitochondria. For concentrations of bound scatterers, the local concentration can be elevated. In cases like imaging RNA in ribosomes, many emitters can be present in a very small volume.

The concentration of NADH in cells is on average about 0.3 mM (29). The free to bound ratio of [NADH] ranges from 1-4. Bound molecules in mitochondria can have concentrations that are significantly higher than average and thus can yield acceptable signals. The concentrations in mitochondria are not precisely known and can vary. Therefore, a signal to noise ratio above about 3 is generally acceptable. To achieve acceptable signals of diffuse distribution of free NADH requires averaging over about 25 pixels or a cube about 5 pixels on a side or a length or about 1μ diameter if they are laid out on a square grid separated by the ½ width of the PSF. The volume is about the same as a single photon STEM system, but since the axial depth is less in MP-STEM the area might be larger or smaller in the plane of focus depending on the pixel layout chosen.

In the backscatter direction, when imaging NADH using STEM for FILM, the noise levels are lower than in the forward direction. There are two major contributions to the background noise:

1) The tissue refractive index gradient backscattering. In cells, the refractive index change between the cytoplasm and nucleus is about 4% which results in a local backscatter of the incident beam [13] or $3\times10^{-4}$ of the incident field.

2) Multiple backscattered probe photons that come through the focal point defining pinhole in the collection aperture. In the system described above, in the backscattered direction the refractive index gradient at the cellular nuclei will produce, at most, about $4.2\times10^9$ backscattered photons in the probe pulses, with shot noise limit of about $6.4\times10^4$.

A pure dipole emitter will emit half the photons in the backward direction. In the example above the ½ width is about 50% of $\lambda_{pr}$ and backscatter is ~9% of the forward scatter. Thus in the 1200 pulses, pixel about 108×n photons are emitted/molecule in the back direction, or about 324 photons when n=3. Thus an SNR=1 at the cytoplasm-nucleus interface requires $1.9\times10^2$ molecules in the focal volume, which is a concentration of 0.03 mM, which is within the concentration range of mammalian tissues. The system would still use lock-in detection techniques as the total system detection sensitivity is still required to be ~$10^4$. Thus high speed dipole-like stimulated backscatter MP-STEM of diffuse or bound NADH molecules is likely to be practical for a 2 pse system.

For 2 pse there is very little dipole emission, thus collection around the focal aperture is required. In this case the detection optics is not in a confocal geometry. The light is collected at high angles around the illumination aperture as shown in the system layout in FIG. 2. Unfortunately, scattered photons from the converging and diverging beam are collected. Therefore, in 2 pse deep tissue imaging, the SNR is degraded as scattered probe photons from the converging beam never make it to focus to participate in stimulate emission, and are not filtered out of the detection system.
Multiphoton Stimulated Fluorescence Lifetime Microscopy (seFLIM)

STEM and MP-STEM can be used to measure the fluorescent lifetime of molecules with multiple decay constants. This method is called stimulated emission Fluorescent Lifetime Microscopy (seFLIM).

SE has been used to measure weak fluorescence by delaying the pump-probe pulse interval, $\Delta t_{pr}$, of only 0.3 ps-1.0 ps in order to limit the rapid non-radiative decay from the excited state. In seFLIM applications $\Delta t_{pr}$ between the pump and probe beams can be varied by additional larger values up to about 5 nsec. As shown in FIG. 11 different probe delays sample different time marks on a fluorescence decay curve.

Two sample $\Delta t_{pr}$ points can be used to determine two unknowns, $N_0$, the initial number of emitters and the fluorescence decay constant $\tau_f$, if there is a single exponential decay of a fluorescent species. These parameters can be calculated turning Eq. 5 into an equation with a time variable as shown in Eq. 23, where $N_0$ is replaced by $(N_0\ e^{-t/\tau_f})$ to compensate for the decay of excited state population prior to stimulated emission probe pulse, and $\tau_f$ is the fluorescence decay constant.

$$\Delta I_{pr}(t) \propto N_0 e^{-t/T} I_{pr}/2(\sigma_{stim[2\to3]}/S) \quad (23)$$

In seFLIM choices of $\Delta t_{pr}$ can include the value of ~500 fs to get the largest signal, and a second value near the fluorescent ½ life of the molecule as shown in FIG. 10.

Many fluorescence decay curves, as discussed above for NAD(P)H in tissue, do not fit a single exponential decay. If M exponential decays are present for M species with the same excitation spectrum, then for each time t, when a probe pulse arrives, the total number excited molecules N(t) is:

$$N(t) = \Sigma_1^M N_m e^{-t/\tau_m} \quad (24)$$

Here, a species m of the M components has $N_m$ molecules at focus and a decay constant $\tau_m$. Thus $\Delta I_{pt}(t)$ in the multicomponent case is defined in Eq. (25):

$$\Delta I_{pt}(t) \propto \left(\sum_1^M N_m e^{-\frac{t}{\tau_m}}\right) I_{pr} \sigma_{stim[2\to3]}/S \quad (25)$$

Eq. 25 can be solved for $\tau m$ and Nm by measuring $\Delta Ipt(t)$ at 2M time points as there are 2M unknowns, M–$N_m$'s and M–$\tau_m$'s, In cases where the decay constants are computed by other means, M time points can determine the concentration of the M species.

SNR in seFLIM is different than standard multiphoton FLIM, where photon counting is used. seFLIM is a bright field technique with high background levels. Therefore information is only available above the noise level as described in the previous section.

In the case of NADH the seFLIM images can be determined by 4-8 images depending the fitting of the data and the accuracy required. FIG. 11 shows multiple time marks that might be used for measuring the fluorescence from bound and unbound NAD(P)H. Examples of potential time points are the following: the first time point with a $\Delta\tau_{pr1}\approx0.5$ ps will measure the maximum gain and total emitter concentration; $\Delta\tau_{pr2}\approx200$-$300$ ps will change by mostly the decay of the free concentration of NAD(P)H; $\Delta\tau_{pr3}\approx1.5$ ns will have practically no contribution from free NAD(P)H and significant decay of the bound NADH; $\Delta\tau_{pr4}\approx3$-$3.5$ ns will measure mostly bound NAD(P)H. In general the bound/free concentration ratio of [NADH]/[NAD], $\alpha_{bound}$, will be ~0.20-0.30, although most of the measured fluorescence comes from the bound compartments because of the longer fluorescent lifetimes. Therefore, the longer probe delays will still display significant signals. The lower noise from dipole-like stimulated emission backscatter can enable fairly rapid seFLIM measurements.

A variable delay is introduced in the probe line to alter the interval between the time of arrival on the pump and probe as shown in FIG. 2. To maximize signal acquisition speeds, the delays can be switched as rapidly as possible. Rapid switching of delays between pulses might enable full seFLIM imaging acquisition in a slowed single image scan.

At high repetition rates in MP-STEM systems, the excited state of long lived fluorophores may not be fully depleted when the next pump-probe pair arrives. For molecules with fluorescence lifetimes of >2 nsec, such as NADPH, this can be a problem. At least 4-6 fluorescent lifetimes between excitations can be allowed in order to depopulate the excited states.

The time sequence of pump and probe beam pulse train signals are shown in FIG. 4. The imaging signal corresponds to the stimulated gain in intensity of the probe beam, computed as the difference between the probe signal from the fluorescent molecular excited state populated by the pump beam, and the un-excited molecular probe signal with the pump beam off. Standard interference filters can be adequate to separate pump and probe photons because they are separate in wavelength by >10 nm. The light is detected in the backward scattered direction by the "epi" light lock-in system. In some applications a standard non lock-in system can be used in the epi direction. In some other applications the signal can be detected in the forward direction.
Metabolic Imaging with MP-STEM In particular it is proposed to use MP-STEM and seFLIM for metabolic imaging of cells and tissues in order to create an energetic picture of normal, diseased and developing tissues. Imaging of the relative amounts of the enzyme cofactors NADH and FAD and the microenvironment of these metabolic electron carriers can be used to noninvasively monitor changes in metabolism, which is one of the hallmarks of carcinogenesis. Also NADH and FAD can be used to assess the state of developing tissues. When bound to metabolic enzymes, NADH fluorescence quantum yield increases, while FAD quantum yield decreases, which causes variation in the measured fluorescence intensities. STEM techniques can measure both bound and unbound cofactor concentration and spatially resolve both molecular states. This can be accomplished by changing the delay between the pump pulse and the Stokes pulses to measure the fluorescent lifetimes of bound and unbound states of a particular chromophore as shown in FIG. 2. The delay of the probe beam can be between 300 femtoseconds and several nanoseconds. The use of STEM and MP-STEM techniques results in image acquisition times that can be more rapid than the use of standard fluorescent lifetime measurements. The hyper resolution of MP-STEM can be used to map the distributions of mitochondria in cells in three dimensions to further characterize the metabolic state of cells and tissues. Furthermore by measuring the short lived and long lived fluorescent lifetimes of NAD(P)H the metabolic state of cells can be determined without the requirement of the use of FAD fluorescence.

MP-STEM can be used to measure the concentrations of molecular species that have multiple fluorescent lifetimes. NAD(P)H can enable deep tissue determination of cellular metabolic state, such as the determination of margins malignant tumors. Deep tissue seFLIM can be able to measure changes in the amounts of cellular melanin types, eumelanin and pheomelanin, that have been associated with carcinogenesis. Eumelanin can serve as anti-oxidant to scavenge free radicals pheomelanin can become a photosensitizer and generate reactive oxygen species after UV radiation. A rapid deep imaging system can be useful in determining the state of differentiation and edges of melanoma tumors.

While this specification contains many specific implementation details, these should not be construed as limitations on the scope of the disclosed technology or of what can be claimed, but rather as descriptions of features specific to particular implementations of the disclosed technology. Certain features that are described in this specification in the context of separate implementations can also be implemented in combination in a single implementation. Conversely, various features that are described in the context of a single implementation can also be implemented in multiple implementations separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In some cases, the actions recited in the claims can be performed in a different order and still achieve desirable results. Moreover, the separation of various system components in the implementations described above should not be understood as requiring such separation in all implementations.

The foregoing Detailed Description is to be understood as being in every respect illustrative, but not restrictive, and the scope of the disclosed technology disclosed herein is not to be determined from the Detailed Description, but rather from the claims as interpreted according to the full breadth permitted by the patent laws. It is to be understood that the implementations shown and described herein are only illustrative of the principles of the disclosed technology and that various modifications can be implemented without departing from the scope and spirit of the disclosed technology.

The invention claimed is:

1. A microscopy system comprising:
a first laser emitting a first laser pulse, the first laser pulse being a pump beam;
a second laser emitting a second laser pulse, the second laser pulse being a probe beam;
a time delay component for delaying the probe beam, wherein the time delay components delay the probe beam by 0.3 ps to 5 ns relative to the pump beam;
an optical device for combining the pump beam and the delayed probe beam into a combined laser pulse, the combined laser pulse having a reduced focal spot size;
a galvanometer scanning system for delivering the combined laser pulse to a focal spot in a focal plane, wherein the reduced focal spot size of the combined laser pulse initiates a stimulated emission of a targeted molecule, the stimulated emission having dipole-like backscatter, and
a detector for detecting the dipole-like backscatter,
wherein at least two photons are used for excitation and at least two photons are used for stimulation emission of a targeted molecule,
wherein an electronic transition from an excited electronic state to a lower energy vibrational ground state is driven by the emission of 2 or more photons at the stimulated emission wavelength, and
wherein the stimulated emission of the targeted molecule is used to measure a metabolic state of cells within tissues via a measurement of a concentration of metabolic cofactors NADH and NADPH, in both free and bound states.

2. The microscopy system of claim 1 wherein the time delay components include an optical switch in the probe beam line to switch the probe beam between at least two delay lines.

3. The microscopy system of claim 2 wherein the optical switch allows at least two different temporal delays between the pump beam and the probe beam, and the microscopy system is configured to calculate molecular fluorescence lifetime.

4. The microscopy system of claim 3 wherein the optical switch is a Mach-Zehnder interferometer.

5. The microscopy system of claim 1 wherein the combined laser pulses are used to excite an electron into an electronic excited state that emit stimulated emission from its lowest energy excited state level.

6. The microscopy system of claim 1 further comprising: an acousto-optic modulator for modulating the pump beam on and off.

7. The microscopy system of claim 6 wherein the detector generates an imaging signal corresponding to a gain in intensity of the probe beam computed as the difference between the combined laser pulse with the pump beam on and the combined laser pulse with the pump beam off.

8. The microscopy system of claim 1 further comprising: a second detector, the second detector detecting forward scatter.

9. A microscopy method comprising the steps of:
emitting a first laser pulse, the first laser pulse being a pump beam;
emitting a second laser pulse, the second laser pulse being a probe beam;
delaying the probe beam, wherein the time delay components delay the probe beam by 0.3 ps to 5 ns relative to the pump beam;
combining the pump beam and the delayed probe beam into a combined laser pulse, the combined laser pulse having a reduced focal spot size;
delivering the combined laser pulse to a focal spot in a focal plane, wherein the reduced focal spot size of the combined laser pulse initiates a stimulated emission of a targeted molecule, the stimulated emission having dipole-like backscatter; and detecting the dipole-like backscatter, wherein at least two photons are used for excitation and at least two photons are used for stimulation emission of a targeted molecule, wherein stimulated emission is measured by recording stimulated emission photons emitted in a multiphoton stimulated transition of a molecule wherein the sum of the energies of the multiple lower energy stimulated emission photons is resonantly about equal to the energy of the fluorescent transition, and wherein the stimulated emission of the targeted molecule is used to measure a metabolic state of cells within tissues via a measurement of a concentration of metabolic cofactors NADH and NADPH, in both free and bound states.

10. The microscopy method of claim 9 wherein an electronic transition from an excited electronic state to a lower energy vibrational ground state is driven by the emission of 2 or more photons at the stimulated emission wavelength.

11. The microscopy method of claim 9 wherein the time delay components include an optical switch in the probe beam line to switch the probe beam between at least two delay lines.

12. The microscopy method of claim 11 wherein the optical switch allows at least two different temporal delays between the pump beam and the probe beam, and calculating molecular fluorescence lifetime.

13. The microscopy method of claim 12 wherein the optical switch is a Mach-Zehnder interferometer.

14. The microscopy method of claim 9 wherein the combined laser pulses are used to excite an electron into an electronic excited state that emit stimulated emission from its lowest energy excited state level.

15. The microscopy method of claim 9 further comprising the step of: modulating the pump beam on and off.

16. The microscopy method of claim 15 further comprising the step of:

generating an imaging signal corresponding to a gain in intensity of the probe beam computed as the difference between the combined laser pulse with the pump beam on and the combined laser pulse with the pump beam off.

17. The microscopy method of claim 9 further comprising the step of:

detecting forward scatter.

* * * * *